(12) United States Patent  (10) Patent No.: US 8,679,158 B2
Leung et al.  (45) Date of Patent: *Mar. 25, 2014

(54) MULTIPLE SUTURE THREAD CONFIGURATION WITH AN INTERMEDIATE CONNECTOR

(75) Inventors: Jeffrey C. Leung, Raleigh, NC (US); Gregory Ruff, Chapel Hill, NC (US); Andrew Kaplan, Hillsborough, NC (US)

(73) Assignee: Ethicon, Inc., Somerville, NJ (US)

( * ) Notice: Subject to any disclaimer, the term of this patent is extended or adjusted under 35 U.S.C. 154(b) by 288 days.

This patent is subject to a terminal disclaimer.

(21) Appl. No.: 12/849,969

(22) Filed: Aug. 4, 2010

(65) Prior Publication Data

US 2011/0009902 A1  Jan. 13, 2011

Related U.S. Application Data

(60) Continuation of application No. 12/119,749, filed on May 13, 2008, now Pat. No. 8,083,770, which is a division of application No. 10/914,755, filed on Aug. 9, 2004, now Pat. No. 7,371,253, which is a division of application No. 10/216,516, filed on Aug. 9, 2002, now Pat. No. 6,773,450.

(51) Int. Cl.
*A61B 17/04* (2006.01)

(52) U.S. Cl.
USPC .......................................... 606/232; 606/329

(58) Field of Classification Search
USPC ......... 606/228, 139, 144, 148, 232, 300, 329, 606/331
See application file for complete search history.

(56) References Cited

U.S. PATENT DOCUMENTS

| | | | |
|---|---|---|---|
| 709,392 | A | 9/1902 | Brown |
| 733,723 | A | 7/1903 | Lukens |
| 789,401 | A | 5/1905 | Acheson |
| 816,026 | A | 3/1906 | Meier |
| 879,758 | A | 2/1908 | Foster |
| 1,142,510 | A | 6/1915 | Engle |
| 1,248,825 | A | 12/1917 | Dederer |
| 1,321,011 | A | 11/1919 | Cottes |
| 1,558,037 | A | 10/1925 | Morton |
| 1,728,316 | A | 9/1929 | Von Wachenfeldt |

(Continued)

FOREIGN PATENT DOCUMENTS

| | | |
|---|---|---|
| BE | 1014364 | 9/2003 |
| CA | 2309844 | 12/1996 |

(Continued)

OTHER PUBLICATIONS

Communication from EPO re: 10000486 dated Apr. 4, 2011.

(Continued)

*Primary Examiner* — Julian Woo

(57) ABSTRACT

A suture system has a plurality of double ended barbed sutures each with a first plurality of barbs located adjacent to a first end and a second plurality of barbs located adjacent to a second end, and a body connector that connects said plurality of double ended barbed sutures. The body connector is located between the first plurality of barbs and the second plurality of barbs on each of the sutures. The sutures can move relative to the body connector. The body connector can retain tissue.

20 Claims, 11 Drawing Sheets

(56) References Cited

U.S. PATENT DOCUMENTS

| | | |
|---|---|---|
| 1,886,721 A | 11/1932 | O'Brien |
| 2,094,578 A | 10/1937 | Blumenthal et al. |
| 2,201,610 A | 5/1940 | Dawson, Jr. |
| 2,232,142 A | 2/1941 | Schumann |
| 2,254,620 A | 9/1941 | Miller |
| 2,347,956 A | 5/1944 | Lansing |
| 2,355,907 A | 8/1944 | Cox |
| 2,421,193 A | 5/1947 | Gardner |
| 2,452,734 A | 11/1948 | Costelow |
| 2,472,009 A | 5/1949 | Gardner |
| 2,480,271 A | 8/1949 | Sumner |
| 2,572,936 A | 10/1951 | Kulp et al. |
| 2,684,070 A | 7/1954 | Kelsey |
| 2,736,964 A | 3/1956 | Lieberman |
| 2,779,083 A | 1/1957 | Enton |
| 2,814,296 A | 11/1957 | Everett |
| 2,817,339 A | 12/1957 | Sullivan |
| 2,866,256 A | 12/1958 | Matlin |
| 2,910,067 A | 10/1959 | White |
| 2,928,395 A | 3/1960 | Forbes et al. |
| 2,988,028 A | 6/1961 | Alcamo |
| 3,003,155 A | 10/1961 | Mielzynski et al. |
| 3,066,452 A | 12/1962 | Bott et al. |
| 3,066,673 A | 12/1962 | Bott et al. |
| 3,068,869 A | 12/1962 | Shelden et al. |
| 3,068,870 A | 12/1962 | Levin |
| 3,123,077 A | 3/1964 | Alcamo |
| 3,166,072 A | 1/1965 | Sullivan, Jr. |
| 3,187,752 A | 6/1965 | Glick |
| 3,206,018 A | 9/1965 | Lewis et al. |
| 3,209,652 A | 10/1965 | Burgsmueller |
| 3,209,754 A | 10/1965 | Brown |
| 3,212,187 A | 10/1965 | Benedict |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,378,010 A | 4/1968 | Codling |
| 3,385,299 A | 5/1968 | LeRoy |
| 3,394,704 A | 7/1968 | Dery |
| 3,494,006 A | 2/1970 | Brumlik |
| 3,522,637 A | 8/1970 | Brumlik |
| 3,525,340 A | 8/1970 | Gilbert |
| 3,527,223 A | 9/1970 | Shein |
| 3,545,608 A | 12/1970 | Berger et al. |
| 3,557,795 A | 1/1971 | Hirsch |
| 3,570,497 A | 3/1971 | Lemole |
| 3,586,002 A | 6/1971 | Wood |
| 3,608,095 A | 9/1971 | Barry |
| 3,608,539 A | 9/1971 | Miller |
| 3,618,447 A | 11/1971 | Goins |
| 3,646,615 A | 3/1972 | Ness |
| 3,683,926 A | 8/1972 | Suzuki |
| 3,700,433 A | 10/1972 | Duhl |
| 3,716,058 A | 2/1973 | Tanner, Jr. |
| 3,720,055 A | 3/1973 | de Mestral et al. |
| 3,748,701 A | 7/1973 | De Mestral |
| 3,762,418 A | 10/1973 | Wasson |
| 3,825,010 A | 7/1974 | McDonald |
| 3,833,972 A | 9/1974 | Brumlik |
| 3,845,641 A | 11/1974 | Waller |
| 3,847,156 A | 11/1974 | Trumble |
| 3,889,322 A | 6/1975 | Brumlik |
| 3,918,455 A | 11/1975 | Coplan |
| 3,922,455 A | 11/1975 | Brumlik |
| 3,941,164 A | 3/1976 | Musgrave |
| 3,951,261 A | 4/1976 | Mandel et al. |
| 3,963,031 A | 6/1976 | Hunter |
| 3,977,937 A | 8/1976 | Candor |
| 3,980,177 A | 9/1976 | McGregor |
| 3,981,051 A | 9/1976 | Brumlik |
| 3,981,307 A | 9/1976 | Borysko |
| 3,985,138 A | 10/1976 | Jarvik |
| 3,985,227 A | 10/1976 | Thyen et al. |
| 3,990,144 A | 11/1976 | Schwartz |
| 4,006,747 A | 2/1977 | Kronenthal |
| 4,008,303 A | 2/1977 | Glick et al. |
| 4,027,608 A | 6/1977 | Arbuckle |
| 4,043,344 A | 8/1977 | Landi |
| 4,052,988 A | 10/1977 | Doddi et al. |
| D246,911 S | 1/1978 | Bess, Jr. et al. |
| 4,069,825 A | 1/1978 | Akiyama |
| 4,073,298 A | 2/1978 | Le Roy |
| 4,137,921 A | 2/1979 | Okuzumi et al. |
| 4,182,340 A | 1/1980 | Spencer |
| 4,186,239 A | 1/1980 | Mize et al. |
| 4,198,734 A | 4/1980 | Brumlik |
| 4,204,541 A | 5/1980 | Kapitanov |
| 4,204,542 A | 5/1980 | Bokros et al. |
| 4,259,959 A | 4/1981 | Walker |
| 4,278,374 A | 7/1981 | Wolosianski |
| 4,300,424 A | 11/1981 | Flinn |
| 4,311,002 A | 1/1982 | Hoffmann et al. |
| 4,313,448 A | 2/1982 | Stokes |
| 4,316,469 A | 2/1982 | Kapitanov |
| 4,317,451 A | 3/1982 | Cerwin et al. |
| 4,372,293 A | 2/1983 | Vijil-Rosales |
| 4,428,376 A | 1/1984 | Mericle |
| 4,430,998 A | 2/1984 | Harvey |
| 4,434,796 A | 3/1984 | Karapetian |
| 4,449,298 A | 5/1984 | Patz |
| 4,454,875 A | 6/1984 | Pratt et al. |
| 4,467,805 A | 8/1984 | Fukuda |
| 4,490,326 A | 12/1984 | Beroff et al. |
| 4,492,075 A | 1/1985 | Faure |
| 4,493,323 A | 1/1985 | Albright et al. |
| 4,505,274 A | 3/1985 | Speelman |
| 4,510,934 A | 4/1985 | Batra |
| 4,531,522 A | 7/1985 | Bedi et al. |
| 4,532,926 A | 8/1985 | O'Holla |
| 4,535,772 A | 8/1985 | Sheehan |
| 4,548,202 A | 10/1985 | Duncan |
| 4,553,544 A | 11/1985 | Nomoto et al. |
| 4,610,250 A | 9/1986 | Green |
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards et al. |
| 4,676,245 A | 6/1987 | Fukuda |
| 4,689,882 A | 9/1987 | Lorenz |
| 4,702,250 A | 10/1987 | Ovil et al. |
| 4,712,553 A | 12/1987 | MacGregor |
| 4,719,917 A | 1/1988 | Barrows |
| 4,741,330 A | 5/1988 | Hayhurst |
| 4,750,910 A | 6/1988 | Takayanagi et al. |
| 4,751,621 A | 6/1988 | Jenkins |
| 4,776,337 A | 10/1988 | Palmaz |
| 4,832,025 A | 5/1989 | Coates |
| 4,841,960 A | 6/1989 | Garner |
| 4,865,026 A | 9/1989 | Barrett |
| 4,873,976 A | 10/1989 | Schreiber |
| 4,887,601 A | 12/1989 | Richards |
| 4,895,148 A | 1/1990 | Bays et al. |
| 4,898,156 A | 2/1990 | Gatturna et al. |
| 4,899,743 A | 2/1990 | Nicholson et al. |
| 4,900,605 A | 2/1990 | Thorgersen et al. |
| 4,905,367 A | 3/1990 | Pinchuk et al. |
| 4,930,945 A | 6/1990 | Arai et al. |
| 4,932,962 A | 6/1990 | Yoon et al. |
| 4,946,468 A | 8/1990 | Li |
| 4,948,444 A | 8/1990 | Schutz et al. |
| 4,950,258 A | 8/1990 | Kawai et al. |
| 4,950,285 A | 8/1990 | Wilk |
| 4,968,315 A | 11/1990 | Gatturna |
| 4,976,715 A | 12/1990 | Bays et al. |
| 4,979,956 A | 12/1990 | Silvestrini |
| 4,981,149 A | 1/1991 | Yoon |
| 4,994,073 A | 2/1991 | Green |
| 4,994,084 A | 2/1991 | Brennan |
| 4,997,439 A | 3/1991 | Chen |
| 5,002,550 A | 3/1991 | Li |
| 5,002,562 A | 3/1991 | Oberlander |

(56) References Cited

U.S. PATENT DOCUMENTS

| | | |
|---|---|---|
| 5,007,921 A | 4/1991 | Brown |
| 5,007,922 A | 4/1991 | Chen et al. |
| 5,026,390 A | 6/1991 | Brown |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,047,047 A | 9/1991 | Yoon |
| 5,053,047 A | 10/1991 | Yoon |
| 5,084,063 A | 1/1992 | Korthoff |
| 5,089,010 A | 2/1992 | Korthoff |
| 5,101,968 A | 4/1992 | Henderson et al. |
| 5,102,418 A | 4/1992 | Granger et al. |
| 5,102,421 A | 4/1992 | Anpach, Jr. |
| 5,103,073 A | 4/1992 | Danilov et al. |
| 5,112,344 A | 5/1992 | Petros |
| 5,123,911 A | 6/1992 | Granger et al. |
| 5,123,913 A | 6/1992 | Wilk et al. |
| 5,123,919 A | 6/1992 | Sauter et al. |
| 5,127,413 A | 7/1992 | Ebert |
| 5,133,738 A | 7/1992 | Korthoff et al. |
| 5,141,520 A | 8/1992 | Goble et al. |
| 5,147,382 A | 9/1992 | Gertzman et al. |
| 5,156,615 A | 10/1992 | Korthoff et al. |
| 5,156,788 A | 10/1992 | Chesterfield et al. |
| 5,176,692 A | 1/1993 | Wilk et al. |
| 5,179,964 A | 1/1993 | Cook |
| 5,192,274 A | 3/1993 | Bierman |
| 5,192,302 A | 3/1993 | Kensey et al. |
| 5,192,303 A | 3/1993 | Gatturna et al. |
| 5,197,597 A | 3/1993 | Leary et al. |
| 5,201,326 A | 4/1993 | Kubicki et al. |
| 5,207,679 A | 5/1993 | Li |
| 5,207,694 A | 5/1993 | Broome |
| 5,217,486 A | 6/1993 | Rice et al. |
| 5,217,494 A | 6/1993 | Coggins et al. |
| 5,222,508 A | 6/1993 | Contarini |
| 5,222,976 A | 6/1993 | Yoon |
| 5,224,946 A | 7/1993 | Hayhurst et al. |
| 5,234,006 A | 8/1993 | Eaton et al. |
| 5,242,457 A | 9/1993 | Akopov et al. |
| 5,246,441 A | 9/1993 | Ross et al. |
| 5,249,673 A | 10/1993 | Sinn |
| 5,258,013 A | 11/1993 | Granger et al. |
| 5,259,846 A | 11/1993 | Granger et al. |
| 5,263,973 A | 11/1993 | Cook |
| 5,269,783 A | 12/1993 | Sander |
| 5,282,832 A | 2/1994 | Toso et al. |
| 5,292,326 A | 3/1994 | Green |
| 5,306,288 A | 4/1994 | Granger et al. |
| 5,306,290 A | 4/1994 | Martins et al. |
| 5,312,422 A | 5/1994 | Trott |
| 5,320,629 A | 6/1994 | Noda et al. |
| 5,330,488 A | 7/1994 | Goldrath |
| 5,330,503 A | 7/1994 | Yoon |
| 5,336,239 A | 8/1994 | Gimpelson |
| 5,341,922 A | 8/1994 | Cerwin et al. |
| 5,342,376 A | 8/1994 | Ruff |
| 5,342,395 A | 8/1994 | Jarrett et al. |
| 5,350,385 A | 9/1994 | Christy |
| 5,352,515 A | 10/1994 | Jarrett et al. |
| 5,354,271 A | 10/1994 | Voda |
| 5,354,298 A | 10/1994 | Lee et al. |
| 5,358,511 A | 10/1994 | Gatturna et al. |
| 5,363,556 A | 11/1994 | Banholzer et al. |
| 5,372,146 A | 12/1994 | Branch |
| 5,374,268 A | 12/1994 | Sander |
| 5,374,278 A | 12/1994 | Chesterfield et al. |
| 5,380,334 A | 1/1995 | Torrie et al. |
| 5,391,173 A | 2/1995 | Wilk |
| 5,395,126 A | 3/1995 | Tresslar |
| 5,403,346 A | 4/1995 | Loeser |
| 5,411,523 A | 5/1995 | Goble |
| 5,414,988 A | 5/1995 | DiPalma et al. |
| 5,417,691 A | 5/1995 | Hayhurst |
| 5,425,746 A | 6/1995 | Proto et al. |
| 5,425,747 A | 6/1995 | Brotz |
| 5,437,680 A | 8/1995 | Yoon et al. |
| 5,450,860 A | 9/1995 | O'Connor |
| 5,451,461 A | 9/1995 | Broyer |
| 5,462,561 A | 10/1995 | Voda |
| 5,464,422 A | 11/1995 | Silverman |
| 5,464,426 A | 11/1995 | Bonutti |
| 5,464,427 A | 11/1995 | Curtis et al. |
| 5,472,452 A | 12/1995 | Trott |
| 5,478,353 A | 12/1995 | Yoon |
| 5,480,403 A | 1/1996 | Lee et al. |
| 5,480,411 A | 1/1996 | Liu et al. |
| 5,484,451 A | 1/1996 | Akopov et al. |
| 5,486,197 A | 1/1996 | Le et al. |
| 5,494,154 A | 2/1996 | Ainsworth et al. |
| 5,500,000 A | 3/1996 | Feagin et al. |
| 5,500,991 A | 3/1996 | Demarest et al. |
| 5,520,084 A | 5/1996 | Chesterfield et al. |
| 5,520,691 A | 5/1996 | Branch |
| 5,522,845 A | 6/1996 | Wenstrom, Jr. |
| 5,527,342 A | 6/1996 | Pietrzak et al. |
| 5,531,760 A | 7/1996 | Alwafaie |
| 5,531,761 A | 7/1996 | Yoon |
| 5,531,790 A | 7/1996 | Frechet et al. |
| 5,533,982 A | 7/1996 | Rizk et al. |
| 5,536,582 A | 7/1996 | Prasad et al. |
| 5,540,705 A | 7/1996 | Meade et al. |
| 5,540,718 A | 7/1996 | Bartlett |
| 5,545,148 A | 8/1996 | Wurster |
| 5,546,957 A | 8/1996 | Heske |
| 5,549,631 A | 8/1996 | Bonutti |
| 5,554,171 A | 9/1996 | Gatturna et al. |
| 5,566,822 A | 10/1996 | Scanlon |
| 5,569,272 A | 10/1996 | Reed et al. |
| 5,571,139 A | 11/1996 | Jenkins, Jr. |
| 5,571,175 A | 11/1996 | Vanney et al. |
| 5,571,216 A | 11/1996 | Anderson |
| 5,573,543 A | 11/1996 | Akopov et al. |
| 5,584,859 A | 12/1996 | Brotz |
| 5,593,424 A | 1/1997 | Northrup, III et al. |
| 5,601,557 A | 2/1997 | Hayhurst |
| 5,626,590 A | 5/1997 | Wilk |
| 5,626,611 A | 5/1997 | Liu et al. |
| 5,632,753 A | 5/1997 | Loeser |
| 5,643,288 A | 7/1997 | Thompson |
| 5,643,295 A | 7/1997 | Yoon |
| 5,643,319 A | 7/1997 | Green et al. |
| 5,645,568 A | 7/1997 | Chervitz et al. |
| 5,647,874 A | 7/1997 | Hayhurst |
| 5,649,939 A | 7/1997 | Reddick |
| 5,653,716 A | 8/1997 | Malo et al. |
| 5,662,714 A | 9/1997 | Charvin et al. |
| 5,669,935 A | 9/1997 | Rosenman et al. |
| 5,676,675 A | 10/1997 | Grice |
| D386,583 S | 11/1997 | Ferragamo et al. |
| 5,683,417 A | 11/1997 | Cooper |
| D387,161 S | 12/1997 | Ferragamo et al. |
| 5,693,072 A | 12/1997 | McIntosh |
| 5,695,879 A | 12/1997 | Goldmann et al. |
| 5,697,976 A | 12/1997 | Chesterfield et al. |
| 5,702,397 A | 12/1997 | Goble et al. |
| 5,702,462 A | 12/1997 | Oberlander |
| 5,709,692 A | 1/1998 | Mollenauer et al. |
| 5,716,358 A | 2/1998 | Ochoa et al. |
| 5,716,376 A | 2/1998 | Roby et al. |
| 5,722,991 A | 3/1998 | Colligan |
| 5,723,008 A | 3/1998 | Gordon |
| 5,725,557 A | 3/1998 | Gatturna et al. |
| 5,728,114 A | 3/1998 | Evans et al. |
| 5,731,855 A | 3/1998 | Koyama et al. |
| 5,741,277 A | 4/1998 | Gordon et al. |
| 5,744,151 A | 4/1998 | Capelli |
| 5,763,411 A | 6/1998 | Edwardson et al. |
| 5,765,560 A | 6/1998 | Verkerke et al. |
| 5,766,246 A | 6/1998 | Mulhauser et al. |
| 5,779,719 A | 7/1998 | Klein et al. |
| 5,782,864 A | 7/1998 | Lizardi |
| 5,807,403 A | 9/1998 | Beyar et al. |

(56) References Cited

U.S. PATENT DOCUMENTS

| | | |
|---|---|---|
| 5,807,406 A | 9/1998 | Brauker et al. |
| 5,810,853 A | 9/1998 | Yoon |
| 5,814,051 A | 9/1998 | Wenstrom, Jr. |
| 5,843,087 A | 12/1998 | Jensen et al. |
| 5,843,178 A | 12/1998 | Vanney et al. |
| 5,855,619 A | 1/1999 | Caplan et al. |
| 5,863,360 A | 1/1999 | Wood et al. |
| 5,884,859 A | 3/1999 | Ma |
| 5,887,594 A | 3/1999 | LoCicero, III |
| 5,891,166 A | 4/1999 | Schervinsky |
| 5,893,856 A | 4/1999 | Jacob et al. |
| 5,895,395 A | 4/1999 | Yeung |
| 5,895,413 A | 4/1999 | Nordstrom |
| 5,897,572 A | 4/1999 | Schulsinger et al. |
| 5,899,911 A | 5/1999 | Carter |
| 5,916,224 A | 6/1999 | Esplin |
| 5,919,234 A | 7/1999 | Lemperle et al. |
| 5,921,982 A | 7/1999 | Lesh et al. |
| 5,925,078 A | 7/1999 | Anderson |
| 5,931,855 A * | 8/1999 | Buncke .................. 606/228 |
| 5,935,138 A | 8/1999 | McJames, II et al. |
| 5,938,668 A | 8/1999 | Scirica et al. |
| 5,941,899 A | 8/1999 | Granger et al. |
| 5,950,633 A | 9/1999 | Lynch et al. |
| 5,954,747 A | 9/1999 | Clark |
| 5,964,765 A | 10/1999 | Fenton, Jr. et al. |
| 5,964,783 A | 10/1999 | Grafton et al. |
| 5,968,097 A | 10/1999 | Frechet et al. |
| 5,972,024 A | 10/1999 | Northrup, III et al. |
| 5,984,933 A | 11/1999 | Yoon |
| 5,993,459 A | 11/1999 | Larsen et al. |
| 6,001,111 A | 12/1999 | Sepetka et al. |
| 6,012,216 A | 1/2000 | Esteves et al. |
| 6,015,410 A | 1/2000 | Tormala et al. |
| 6,024,757 A | 2/2000 | Haase et al. |
| 6,027,523 A | 2/2000 | Schmieding |
| 6,039,741 A | 3/2000 | Meislin |
| 5,320,629 B1 | 5/2000 | Noda et al. |
| 6,056,778 A | 5/2000 | Grafton et al. |
| 6,063,105 A | 5/2000 | Totakura |
| 6,071,292 A | 6/2000 | Makower et al. |
| 6,074,419 A | 6/2000 | Healy et al. |
| 6,076,255 A | 6/2000 | Shikakubo et al. |
| 6,083,244 A | 7/2000 | Lubbers et al. |
| 6,102,947 A | 8/2000 | Gordon |
| 6,106,544 A | 8/2000 | Brazeau |
| 6,106,545 A | 8/2000 | Egan |
| 6,110,484 A | 8/2000 | Sierra |
| 6,129,741 A | 10/2000 | Wurster et al. |
| D433,753 S | 11/2000 | Weiss |
| 6,146,406 A | 11/2000 | Shluzas et al. |
| 6,146,407 A | 11/2000 | Krebs |
| 6,149,660 A | 11/2000 | Laufer et al. |
| 6,159,234 A | 12/2000 | Bonutti et al. |
| 6,160,084 A | 12/2000 | Langer et al. |
| 6,163,948 A | 12/2000 | Esteves et al. |
| 6,165,203 A | 12/2000 | Krebs |
| 6,168,633 B1 | 1/2001 | Shoher et al. |
| 6,174,324 B1 | 1/2001 | Egan et al. |
| 6,183,499 B1 | 2/2001 | Fischer et al. |
| 6,187,095 B1 | 2/2001 | Labrecque et al. |
| 6,203,565 B1 | 3/2001 | Bonutti et al. |
| 6,206,908 B1 | 3/2001 | Roby |
| 6,214,030 B1 | 4/2001 | Matsutani et al. |
| 6,231,911 B1 | 5/2001 | Steinback et al. |
| 6,235,869 B1 | 5/2001 | Roby et al. |
| 6,241,747 B1 | 6/2001 | Ruff |
| 6,251,143 B1 | 6/2001 | Schwartz et al. |
| 6,264,675 B1 | 7/2001 | Brotz |
| 6,267,772 B1 | 7/2001 | Mulhauser et al. |
| 6,270,517 B1 | 8/2001 | Brotz |
| 6,315,788 B1 | 11/2001 | Roby |
| 6,319,231 B1 | 11/2001 | Andrulitis |
| 6,322,581 B1 | 11/2001 | Fukuda et al. |
| 6,334,865 B1 | 1/2002 | Redmond et al. |
| 6,383,201 B1 | 5/2002 | Dong |
| 6,387,363 B1 | 5/2002 | Gruskin |
| 6,388,043 B1 | 5/2002 | Langer et al. |
| 6,395,029 B1 | 5/2002 | Levy |
| D462,766 S | 9/2002 | Jacobs et al. |
| 6,443,962 B1 | 9/2002 | Gaber |
| 6,463,719 B2 | 10/2002 | Dey et al. |
| 6,471,715 B1 | 10/2002 | Weiss |
| 6,478,809 B1 | 11/2002 | Brotz |
| 6,485,503 B2 | 11/2002 | Jacobs et al. |
| 6,491,701 B2 | 12/2002 | Tierney et al. |
| 6,491,714 B1 | 12/2002 | Bennett |
| 6,494,898 B1 | 12/2002 | Roby et al. |
| 6,495,127 B1 | 12/2002 | Wallace et al. |
| RE37,963 E | 1/2003 | Thal |
| 6,506,190 B1 | 1/2003 | Walshe |
| 6,506,197 B1 | 1/2003 | Rollero et al. |
| 6,511,488 B1 | 1/2003 | Marshall et al. |
| 6,514,265 B2 | 2/2003 | Ho et al. |
| 6,527,795 B1 | 3/2003 | Lizardi |
| 6,548,002 B2 | 4/2003 | Gresser et al. |
| 6,548,569 B1 | 4/2003 | Williams et al. |
| 6,551,343 B1 | 4/2003 | Tormala et al. |
| 6,554,802 B1 | 4/2003 | Pearson et al. |
| 6,565,597 B1 | 5/2003 | Fearnot et al. |
| 6,592,609 B1 | 7/2003 | Bonutti |
| 6,596,296 B1 | 7/2003 | Nelson et al. |
| 6,599,310 B2 | 7/2003 | Leung et al. |
| 6,607,541 B1 | 8/2003 | Gardiner et al. |
| 6,610,078 B1 | 8/2003 | Bru-Magniez et al. |
| 6,613,059 B2 | 9/2003 | Schaller et al. |
| 6,613,254 B1 | 9/2003 | Shiffer |
| 6,616,982 B2 | 9/2003 | Merrill et al. |
| 6,623,492 B1 | 9/2003 | Berube et al. |
| 6,626,930 B1 | 9/2003 | Allen et al. |
| 6,632,245 B2 * | 10/2003 | Kim .................. 606/232 |
| 6,641,592 B1 | 11/2003 | Sauer et al. |
| 6,641,593 B1 | 11/2003 | Schaller et al. |
| 6,645,226 B1 | 11/2003 | Jacobs et al. |
| 6,645,227 B2 | 11/2003 | Fallin et al. |
| 6,645,228 B2 | 11/2003 | Renz |
| 6,648,921 B2 | 11/2003 | Anderson et al. |
| 6,656,182 B1 | 12/2003 | Hayhurst |
| 6,689,153 B1 | 2/2004 | Skiba |
| 6,689,166 B2 | 2/2004 | Laurencin et al. |
| 6,692,761 B2 | 2/2004 | Mahmood et al. |
| 6,702,844 B1 | 3/2004 | Lazarus |
| 6,712,830 B2 | 3/2004 | Esplin |
| 6,716,234 B2 | 4/2004 | Grafton et al. |
| 6,720,402 B2 | 4/2004 | Langer et al. |
| 6,726,705 B2 | 4/2004 | Peterson et al. |
| 6,746,443 B1 | 6/2004 | Morley et al. |
| 6,746,458 B1 | 6/2004 | Cloud |
| 6,749,616 B1 | 6/2004 | Nath |
| 6,773,450 B2 | 8/2004 | Leung et al. |
| 6,783,554 B2 | 8/2004 | Amara et al. |
| 6,814,748 B1 | 11/2004 | Baker et al. |
| 6,818,010 B2 | 11/2004 | Eichhorn et al. |
| 6,838,493 B2 | 1/2005 | Williams et al. |
| 6,848,152 B2 | 2/2005 | Genova et al. |
| 6,852,825 B2 | 2/2005 | Ledlein et al. |
| 6,858,222 B2 | 2/2005 | Nelson et al. |
| 6,860,891 B2 | 3/2005 | Schulze |
| 6,860,901 B1 | 3/2005 | Baker et al. |
| 6,867,248 B1 | 3/2005 | Martin et al. |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman et al. |
| 6,911,035 B1 | 6/2005 | Blomme |
| 6,911,037 B2 | 6/2005 | Gainor et al. |
| 6,913,607 B2 | 7/2005 | Ainsworth et al. |
| 6,921,811 B2 | 7/2005 | Zamora et al. |
| 6,923,819 B2 | 8/2005 | Meade et al. |
| 6,945,021 B2 | 9/2005 | Michel |
| 6,945,980 B2 | 9/2005 | Nguyen et al. |
| 6,960,221 B2 | 11/2005 | Ho et al. |
| 6,960,233 B1 | 11/2005 | Berg et al. |
| 6,974,450 B2 | 12/2005 | Weber et al. |

(56) References Cited

U.S. PATENT DOCUMENTS

| | | |
|---|---|---|
| 6,981,983 B1 | 1/2006 | Rosenblatt et al. |
| 6,984,241 B2 | 1/2006 | Lubbers et al. |
| 6,986,780 B2 | 1/2006 | Rudnick et al. |
| 6,991,643 B2 | 1/2006 | Saadat |
| 6,996,880 B2 | 2/2006 | Kurtz, Jr. |
| 7,021,316 B2 | 4/2006 | Leiboff |
| 7,033,379 B2 | 4/2006 | Peterson |
| 7,033,603 B2 | 4/2006 | Nelson et al. |
| 7,037,984 B2 | 5/2006 | Ledlein et al. |
| 7,048,748 B1 | 5/2006 | Ustuner |
| 7,056,331 B2 | 6/2006 | Kaplan et al. |
| 7,056,333 B2 | 6/2006 | Walshe |
| 7,057,135 B2 | 6/2006 | Li |
| 7,063,716 B2 | 6/2006 | Cunningham |
| 7,070,610 B2 | 7/2006 | Im et al. |
| 7,081,135 B2 | 7/2006 | Smith et al. |
| 7,083,637 B1 | 8/2006 | Tannhauser |
| 7,083,648 B2 | 8/2006 | Yu et al. |
| 7,107,090 B2 | 9/2006 | Salisbury, Jr. et al. |
| 7,112,214 B2 | 9/2006 | Peterson et al. |
| 7,125,403 B2 | 10/2006 | Julian et al. |
| 7,125,413 B2 | 10/2006 | Grigoryants et al. |
| D532,107 S | 11/2006 | Peterson et al. |
| 7,138,441 B1 | 11/2006 | Zhang |
| 7,141,302 B2 | 11/2006 | Mueller et al. |
| 7,144,401 B2 | 12/2006 | Yamamoto et al. |
| 7,144,412 B2 | 12/2006 | Wolf et al. |
| 7,144,415 B2 | 12/2006 | DelRio et al. |
| 7,150,757 B2 | 12/2006 | Fallin et al. |
| 7,156,858 B2 | 1/2007 | Schuldt-Hempe et al. |
| 7,156,862 B2 | 1/2007 | Jacobs et al. |
| 7,160,312 B2 | 1/2007 | Saadat |
| 7,166,570 B2 | 1/2007 | Hunter et al. |
| 7,172,595 B1 | 2/2007 | Goble |
| 7,172,615 B2 | 2/2007 | Morriss et al. |
| 7,186,262 B2 | 3/2007 | Saadat |
| 7,195,634 B2 | 3/2007 | Schmieding et al. |
| 7,211,088 B2 | 5/2007 | Grafton et |
| 7,214,230 B2 | 5/2007 | Brock et al. |
| 7,217,744 B2 | 5/2007 | Lendlein et al. |
| 7,225,512 B2 | 6/2007 | Genova et al. |
| 7,226,468 B2 | 6/2007 | Ruff |
| 7,232,447 B2 | 6/2007 | Gellman et al. |
| 7,244,270 B2 | 7/2007 | Lesh et al. |
| 7,279,612 B1 | 10/2007 | Heaton et al. |
| 7,297,142 B2 | 11/2007 | Brock |
| 7,322,105 B2 | 1/2008 | Lewis |
| 7,371,253 B2 | 5/2008 | Leung et al. |
| 7,513,904 B2 | 4/2009 | Sulamanidze et al. |
| 7,514,095 B2 | 4/2009 | Nelson et al. |
| 7,582,105 B2 | 9/2009 | Kolster |
| 7,601,164 B2 | 10/2009 | Wu |
| 7,624,487 B2 | 12/2009 | Trull et al. |
| 7,806,908 B2 | 10/2010 | Ruff |
| 7,845,356 B2 | 12/2010 | Paraschac et al. |
| 7,857,829 B2 | 12/2010 | Kaplan et al. |
| 7,879,072 B2* | 2/2011 | Bonutti et al. ............... 606/232 |
| 8,118,834 B1 | 2/2012 | Goraltchouk et al. |
| 8,216,273 B1 | 7/2012 | Goraltchouk et al. |
| 2001/0011187 A1 | 8/2001 | Pavcnik et al. |
| 2001/0018592 A1 | 8/2001 | Schaller et al. |
| 2001/0018599 A1 | 8/2001 | D'Aversa et al. |
| 2001/0039450 A1 | 11/2001 | Pavcnik et al. |
| 2001/0044637 A1 | 11/2001 | Jacobs et al. |
| 2001/0051807 A1 | 12/2001 | Grafton |
| 2001/0051815 A1 | 12/2001 | Esplin |
| 2002/0007218 A1 | 1/2002 | Cauthen |
| 2002/0022861 A1 | 2/2002 | Jacobs et al. |
| 2002/0029011 A1 | 3/2002 | Dyer |
| 2002/0029066 A1 | 3/2002 | Foerster |
| 2002/0069617 A1 | 6/2002 | Dey et al. |
| 2002/0077448 A1 | 6/2002 | Antal et al. |
| 2002/0077631 A1 | 6/2002 | Lubbers et al. |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0138009 A1 | 9/2002 | Brockway et al. |
| 2002/0151932 A1 | 10/2002 | Bryant et al. |
| 2002/0151980 A1 | 10/2002 | Cauthen |
| 2002/0161168 A1 | 10/2002 | Shalaby et al. |
| 2002/0173807 A1 | 11/2002 | Jacobs |
| 2002/0173822 A1 | 11/2002 | Justin et al. |
| 2002/0179718 A1 | 12/2002 | Murokh et al. |
| 2003/0014077 A1 | 1/2003 | Leung et al. |
| 2003/0040795 A1 | 2/2003 | Elson et al. |
| 2003/0041426 A1 | 3/2003 | Genova et al. |
| 2003/0065360 A1 | 4/2003 | Jacobs et al. |
| 2003/0065402 A1 | 4/2003 | Anderson et al. |
| 2003/0069602 A1 | 4/2003 | Jacobs et al. |
| 2003/0074021 A1 | 4/2003 | Morriss et al. |
| 2003/0074023 A1 | 4/2003 | Kaplan et al. |
| 2003/0078604 A1 | 4/2003 | Walshe |
| 2003/0088270 A1 | 5/2003 | Lubbers et al. |
| 2003/0097150 A1 | 5/2003 | Fallin et al. |
| 2003/0105489 A1 | 6/2003 | Eichhorn et al. |
| 2003/0149447 A1 | 8/2003 | Morency |
| 2003/0158604 A1 | 8/2003 | Cauthen, III et al. |
| 2003/0167072 A1 | 9/2003 | Oberlander |
| 2003/0199923 A1 | 10/2003 | Khairkhahan et al. |
| 2003/0203003 A1 | 10/2003 | Nelson et al. |
| 2003/0204193 A1 | 10/2003 | Gabriel et al. |
| 2003/0204195 A1 | 10/2003 | Keane et al. |
| 2003/0225424 A1 | 12/2003 | Benderev |
| 2003/0229361 A1 | 12/2003 | Jackson |
| 2003/0236550 A1 | 12/2003 | Peterson et al. |
| 2003/0236551 A1 | 12/2003 | Peterson |
| 2004/0006353 A1 | 1/2004 | Bosley, Jr. et al. |
| 2004/0010275 A1 | 1/2004 | Jacobs et al. |
| 2004/0010276 A1 | 1/2004 | Jacobs et al. |
| 2004/0015187 A1 | 1/2004 | Lendlein et al. |
| 2004/0024169 A1 | 2/2004 | Shalaby et al. |
| 2004/0024420 A1 | 2/2004 | Lubbers et al. |
| 2004/0028655 A1 | 2/2004 | Nelson et al. |
| 2004/0030354 A1 | 2/2004 | Leung et al. |
| 2004/0039415 A1 | 2/2004 | Zamierowski |
| 2004/0049224 A1 | 3/2004 | Buehlmann et al. |
| 2004/0059370 A1 | 3/2004 | Greene, Jr. et al. |
| 2004/0059377 A1 | 3/2004 | Peterson et al. |
| 2004/0059378 A1 | 3/2004 | Peterson et al. |
| 2004/0060409 A1 | 4/2004 | Leung et al. |
| 2004/0060410 A1 | 4/2004 | Leung et al. |
| 2004/0068293 A1 | 4/2004 | Scalzo et al. |
| 2004/0068294 A1 | 4/2004 | Scalzo et al. |
| 2004/0088003 A1 | 5/2004 | Leung et al. |
| 2004/0093023 A1 | 5/2004 | Allen et al. |
| 2004/0093028 A1 | 5/2004 | Ruff |
| 2004/0098051 A1 | 5/2004 | Fallin et al. |
| 2004/0106949 A1 | 6/2004 | Cohn et al. |
| 2004/0116620 A1 | 6/2004 | Shalaby et al. |
| 2004/0138683 A1 | 7/2004 | Shelton et al. |
| 2004/0153153 A1 | 8/2004 | Elson et al. |
| 2004/0167572 A1 | 8/2004 | Roth et al. |
| 2004/0167575 A1 | 8/2004 | Roby |
| 2004/0186487 A1 | 9/2004 | Klein et al. |
| 2004/0193191 A1 | 9/2004 | Starksen et al. |
| 2004/0193217 A1 | 9/2004 | Lubbers et al. |
| 2004/0193257 A1 | 9/2004 | Wu et al. |
| 2004/0226427 A1 | 11/2004 | Trull et al. |
| 2004/0230223 A1 | 11/2004 | Bonutti et al. |
| 2004/0237736 A1 | 12/2004 | Genova et al. |
| 2004/0254609 A1 | 12/2004 | Esplin |
| 2004/0260340 A1 | 12/2004 | Jacobs et al. |
| 2004/0265282 A1 | 12/2004 | Wright et al. |
| 2004/0267309 A1 | 12/2004 | Garvin |
| 2005/0004601 A1 | 1/2005 | Kong et al. |
| 2005/0004602 A1 | 1/2005 | Hart et al. |
| 2005/0033324 A1 | 2/2005 | Phan |
| 2005/0033367 A1 | 2/2005 | Leung et al. |
| 2005/0034431 A1 | 2/2005 | Dey et al. |
| 2005/0038472 A1 | 2/2005 | Furst |
| 2005/0049636 A1 | 3/2005 | Leiboff |
| 2005/0055051 A1 | 3/2005 | Grafton |
| 2005/0059984 A1 | 3/2005 | Chanduszko et al. |

(56) References Cited

U.S. PATENT DOCUMENTS

| | | |
|---|---|---|
| 2005/0065533 A1 | 3/2005 | Magen et al. |
| 2005/0070959 A1 | 3/2005 | Cichocki, Jr. |
| 2005/0080455 A1 | 4/2005 | Schmieding et al. |
| 2005/0085857 A1 | 4/2005 | Peterson et al. |
| 2005/0096698 A1 | 5/2005 | Lederman |
| 2005/0106211 A1 | 5/2005 | Nelson et al. |
| 2005/0113936 A1 | 5/2005 | Brustad et al. |
| 2005/0119694 A1 | 6/2005 | Jacobs et al. |
| 2005/0125020 A1 | 6/2005 | Meade et al. |
| 2005/0125034 A1 | 6/2005 | Cichocki, Jr. |
| 2005/0125035 A1 | 6/2005 | Cichocki, Jr. |
| 2005/0149064 A1 | 7/2005 | Peterson et al. |
| 2005/0149118 A1 | 7/2005 | Koyfman et al. |
| 2005/0154255 A1 | 7/2005 | Jacobs |
| 2005/0171561 A1 | 8/2005 | Songer et al. |
| 2005/0177190 A1 | 8/2005 | Zamierowski |
| 2005/0181009 A1 | 8/2005 | Hunter et al. |
| 2005/0182444 A1 | 8/2005 | Peterson et al. |
| 2005/0182445 A1 | 8/2005 | Zamierowski |
| 2005/0186247 A1 | 8/2005 | Hunter et al. |
| 2005/0197699 A1 | 9/2005 | Jacobs et al. |
| 2005/0199249 A1 | 9/2005 | Karram |
| 2005/0203576 A1 | 9/2005 | Sulamandize et al. |
| 2005/0209542 A1 | 9/2005 | Jacobs et al. |
| 2005/0209612 A1 | 9/2005 | Nakao |
| 2005/0234510 A1 | 10/2005 | Zamierowski |
| 2005/0240220 A1 | 10/2005 | Zamierowski |
| 2005/0240224 A1 | 10/2005 | Wu |
| 2005/0267531 A1 | 12/2005 | Ruff et al. |
| 2005/0267532 A1 | 12/2005 | Wu |
| 2005/0277984 A1 | 12/2005 | Long |
| 2005/0283246 A1 | 12/2005 | Cauthen, III et al. |
| 2006/0020272 A1 | 1/2006 | Gildenberg |
| 2006/0030884 A1 | 2/2006 | Young et al. |
| 2006/0036266 A1 | 2/2006 | Sulamanidze et al. |
| 2006/0058470 A1 | 3/2006 | Rizk |
| 2006/0058574 A1 | 3/2006 | Priewe et al. |
| 2006/0058799 A1 | 3/2006 | Elson et al. |
| 2006/0058844 A1 | 3/2006 | White et al. |
| 2006/0063476 A1 | 3/2006 | Dore |
| 2006/0064115 A1 | 3/2006 | Allen et al. |
| 2006/0064116 A1 | 3/2006 | Allen et al. |
| 2006/0064127 A1 | 3/2006 | Fallin et al. |
| 2006/0079469 A1 | 4/2006 | Anderson et al. |
| 2006/0079935 A1 | 4/2006 | Kolster |
| 2006/0085016 A1 | 4/2006 | Eremia |
| 2006/0089525 A1 | 4/2006 | Mamo et al. |
| 2006/0089672 A1 | 4/2006 | Martinek |
| 2006/0111734 A1 | 5/2006 | Kaplan et al. |
| 2006/0111742 A1 | 5/2006 | Kaplan et al. |
| 2006/0116503 A1 | 6/2006 | Lendlein et al. |
| 2006/0122608 A1 | 6/2006 | Fallin et al. |
| 2006/0135994 A1 | 6/2006 | Ruff |
| 2006/0135995 A1 | 6/2006 | Ruff |
| 2006/0140999 A1 | 6/2006 | Lendlein et al. |
| 2006/0142784 A1 | 6/2006 | Kontos |
| 2006/0193769 A1 | 8/2006 | Nelson et al. |
| 2006/0194721 A1 | 8/2006 | Allen |
| 2006/0200062 A1 | 9/2006 | Saadat |
| 2006/0207612 A1 | 9/2006 | Jackson et al. |
| 2006/0229671 A1 | 10/2006 | Steiner et al. |
| 2006/0235445 A1 | 10/2006 | Birk et al. |
| 2006/0235447 A1 | 10/2006 | Walshe |
| 2006/0235516 A1 | 10/2006 | Cavazzoni |
| 2006/0241658 A1 | 10/2006 | Cerundolo |
| 2006/0249405 A1 | 11/2006 | Cerwin et al. |
| 2006/0253126 A1 | 11/2006 | Bjerken et al. |
| 2006/0257629 A1 | 11/2006 | Ledlein et al. |
| 2006/0258938 A1 | 11/2006 | Hoffman et al. |
| 2006/0272979 A1 | 12/2006 | Lubbers et al. |
| 2006/0276808 A1 | 12/2006 | Arnal et al. |
| 2006/0282099 A1 | 12/2006 | Stokes et al. |
| 2006/0286289 A1 | 12/2006 | Prajapati et al. |
| 2006/0287675 A1 | 12/2006 | Prajapati et al. |
| 2006/0287676 A1 | 12/2006 | Prajapati et al. |
| 2006/0293710 A1 | 12/2006 | Foerster et al. |
| 2007/0005109 A1 | 1/2007 | Popadiuk et al. |
| 2007/0005110 A1 | 1/2007 | Collier et al. |
| 2007/0021779 A1 | 1/2007 | Garvin et al. |
| 2007/0027475 A1 | 2/2007 | Pagedas |
| 2007/0038249 A1 | 2/2007 | Kolster |
| 2007/0065663 A1 | 3/2007 | Trull et al. |
| 2007/0088135 A1 | 4/2007 | Lendlein et al. |
| 2007/0088391 A1 | 4/2007 | McAlexander et al. |
| 2007/0134292 A1 | 6/2007 | Suokas et al. |
| 2007/0135840 A1 | 6/2007 | Schmieding |
| 2007/0135843 A1 | 6/2007 | Burkhart |
| 2007/0151961 A1 | 7/2007 | Kleine et al. |
| 2007/0156175 A1 | 7/2007 | Weadock et al. |
| 2007/0167958 A1 | 7/2007 | Sulamanidze et al. |
| 2007/0187861 A1 | 8/2007 | Geneva et al. |
| 2007/0208355 A1 | 9/2007 | Ruff |
| 2007/0208377 A1 | 9/2007 | Kaplan et al. |
| 2007/0219587 A1 | 9/2007 | Accardo |
| 2007/0224237 A1 | 9/2007 | Hwang et al. |
| 2007/0225642 A1 | 9/2007 | Houser et al. |
| 2007/0225761 A1 | 9/2007 | Shetty |
| 2007/0227914 A1 | 10/2007 | Cerwin et al. |
| 2007/0233188 A1 | 10/2007 | Hunt et al. |
| 2007/0239206 A1 | 10/2007 | Shelton, IV et al. |
| 2007/0239207 A1 | 10/2007 | Beramendi |
| 2007/0257395 A1 | 11/2007 | Lindh et al. |
| 2007/0282247 A1 | 12/2007 | Desai et al. |
| 2008/0004490 A1 | 1/2008 | Bosley, Jr. et al. |
| 2008/0004603 A1 | 1/2008 | Larkin et al. |
| 2008/0009838 A1 | 1/2008 | Schena et al. |
| 2008/0009888 A1 | 1/2008 | Ewers et al. |
| 2008/0009902 A1 | 1/2008 | Hunter et al. |
| 2008/0027273 A1 | 1/2008 | Gutterman |
| 2008/0027486 A1 | 1/2008 | Jones et al. |
| 2008/0046094 A1 | 2/2008 | Han et al. |
| 2008/0058869 A1 | 3/2008 | Stopek et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0077181 A1 | 3/2008 | Jones et al. |
| 2008/0082113 A1 | 4/2008 | Bishop et al. |
| 2008/0082129 A1 | 4/2008 | Jones et al. |
| 2008/0086169 A1 | 4/2008 | Jones et al. |
| 2008/0086170 A1 | 4/2008 | Jones et al. |
| 2008/0109036 A1 | 5/2008 | Stopek et al. |
| 2008/0132943 A1 | 6/2008 | Maiorino et al. |
| 2008/0195417 A1 | 8/2008 | Surpin et al. |
| 2008/0208358 A1 | 8/2008 | Bellamkonda et al. |
| 2008/0215072 A1 | 9/2008 | Kelly |
| 2008/0221618 A1 | 9/2008 | Chen et al. |
| 2008/0234731 A1 | 9/2008 | Leung et al. |
| 2008/0248216 A1 | 10/2008 | Yeung et al. |
| 2008/0255611 A1 | 10/2008 | Hunter |
| 2008/0262542 A1 | 10/2008 | Sulamanidze et al. |
| 2008/0281338 A1 | 11/2008 | Wohlert et al. |
| 2008/0312688 A1 | 12/2008 | Nawrocki et al. |
| 2009/0012560 A1 | 1/2009 | Hunter et al. |
| 2009/0018577 A1 | 1/2009 | Leung et al. |
| 2009/0043336 A1 | 2/2009 | Yuan et al. |
| 2009/0076543 A1 | 3/2009 | Maiorino et al. |
| 2009/0099597 A1 | 4/2009 | Isse |
| 2009/0107965 A1 | 4/2009 | D'Agostino |
| 2009/0112259 A1 | 4/2009 | D'Agostino |
| 2009/0143819 A1 | 6/2009 | D'Agostino |
| 2009/0200487 A1 | 8/2009 | Maiorino et al. |
| 2009/0210006 A1 | 8/2009 | Cohen et al. |
| 2009/0226500 A1 | 9/2009 | Avelar et al. |
| 2009/0248066 A1 | 10/2009 | Wilkie |
| 2009/0248067 A1 | 10/2009 | Maiorino |
| 2009/0248070 A1 | 10/2009 | Kosa et al. |
| 2009/0250356 A1 | 10/2009 | Kirsch et al. |
| 2009/0259233 A1 | 10/2009 | Bogart et al. |
| 2009/0259251 A1 | 10/2009 | Cohen |
| 2009/0287245 A1 | 11/2009 | Ostrovsky et al. |
| 2009/0299407 A1 | 12/2009 | Yuan et al. |
| 2009/0299408 A1 | 12/2009 | Schuldt-Hempe et al. |
| 2009/0306710 A1 | 12/2009 | Lindh et al. |

(56) References Cited

U.S. PATENT DOCUMENTS

| | | |
|---|---|---|
| 2010/0023055 A1 | 1/2010 | Rousseau |
| 2010/0057123 A1 | 3/2010 | D'Agostino et al. |
| 2010/0063540 A1 | 3/2010 | Maiorino |
| 2010/0071833 A1 | 3/2010 | Maiorino |
| 2010/0087855 A1 | 4/2010 | Leung et al. |
| 2010/0101707 A1 | 4/2010 | Maiorino et al. |
| 2010/0140115 A1 | 6/2010 | Kirsch |
| 2010/0230300 A1 | 9/2010 | Hunter et al. |
| 2010/0294103 A1 | 11/2010 | Genova et al. |
| 2010/0294104 A1 | 11/2010 | Genova et al. |
| 2010/0294105 A1 | 11/2010 | Genova et al. |
| 2010/0294106 A1 | 11/2010 | Genova et al. |
| 2010/0294107 A1 | 11/2010 | Genova et al. |
| 2010/0298637 A1 | 11/2010 | Ruff |
| 2010/0298639 A1 | 11/2010 | Leung et al. |
| 2010/0298867 A1 | 11/2010 | Ruff |
| 2010/0298868 A1 | 11/2010 | Ruff |
| 2010/0298871 A1 | 11/2010 | Ruff et al. |
| 2010/0298878 A1 | 11/2010 | Leung et al. |
| 2010/0298879 A1 | 11/2010 | Leung et al. |
| 2010/0298880 A1 | 11/2010 | Leung et al. |
| 2010/0313723 A1 | 12/2010 | Genova et al. |
| 2010/0313729 A1 | 12/2010 | Genova et al. |
| 2010/0313730 A1 | 12/2010 | Genova et al. |
| 2010/0318122 A1 | 12/2010 | Leung et al. |
| 2010/0318123 A1 | 12/2010 | Leung et al. |
| 2010/0318124 A1 | 12/2010 | Leung et al. |
| 2011/0009902 A1 | 1/2011 | Leung et al. |
| 2011/0046669 A1 | 2/2011 | Goraltchouk et al. |
| 2011/0106152 A1 | 5/2011 | Kozlowski |
| 2011/0130774 A1 | 6/2011 | Criscuolo et al. |
| 2011/0166597 A1 | 7/2011 | Herrmann et al. |

FOREIGN PATENT DOCUMENTS

| | | |
|---|---|---|
| CN | 2640420 | 9/2004 |
| DE | 01810800 | 6/1970 |
| DE | 03227984 | 2/1984 |
| DE | 04302895 | 8/1994 |
| DE | 19618891 | 4/1997 |
| DE | 19833703 | 2/2000 |
| DE | 10245025 | 4/2004 |
| DE | 102005004317 | 6/2006 |
| EP | 0121362 | 9/1987 |
| EP | 0329787 | 8/1989 |
| EP | 0513713 | 5/1992 |
| EP | 0428253 | 7/1994 |
| EP | 0632999 | 1/1995 |
| EP | 0513736 | 2/1995 |
| EP | 0464479 | 3/1995 |
| EP | 0464480 | 3/1995 |
| EP | 0576337 | 3/1997 |
| EP | 0574707 | 8/1997 |
| EP | 0612504 | 11/1997 |
| EP | 0558993 | 4/1998 |
| EP | 0913123 | 5/1999 |
| EP | 0916310 | 5/1999 |
| EP | 0664198 | 6/1999 |
| EP | 0960600 | 12/1999 |
| EP | 0705567 | 3/2002 |
| EP | 0673624 | 8/2002 |
| EP | 0839499 | 9/2003 |
| EP | 0755656 | 12/2003 |
| EP | 1075843 | 2/2005 |
| EP | 1525851 | 4/2005 |
| EP | 1532942 | 5/2005 |
| EP | 0826337 | 12/2005 |
| EP | 0991359 | 11/2007 |
| EP | 2036502 | 3/2009 |
| EP | 1726317 | 7/2012 |
| EP | 2338421 | 11/2012 |
| FR | 2619129 | 2/1989 |
| FR | 2693108 | 1/1994 |
| FR | 9208059 | 3/1997 |
| GB | 0267007 | 3/1927 |
| GB | 1091282 | 11/1967 |
| GB | 1428560 | 7/1973 |
| GB | 1506362 | 4/1978 |
| GB | 1508627 | 4/1978 |
| JP | 51-130091 | 11/1976 |
| JP | 1506362 | 4/1978 |
| JP | 054116419 | 9/1979 |
| JP | 63-500702 | 3/1988 |
| JP | 63288146 | 11/1988 |
| JP | 001113091 | 5/1989 |
| JP | 003-165751 | 7/1991 |
| JP | 4-96758 | 3/1992 |
| JP | 4-226642 | 8/1992 |
| JP | 004-266749 | 9/1992 |
| JP | 10-503389 | 11/1995 |
| JP | 9-103477 | 4/1997 |
| JP | 410085225 | 4/1998 |
| JP | 10-511009 | 10/1998 |
| JP | 11-313826 | 11/1999 |
| JP | 011332828 | 12/1999 |
| JP | 2002-59235 | 2/2002 |
| JP | 2002-511308 | 4/2002 |
| JP | 2003-275217 | 9/2003 |
| JP | 2004-530524 | 10/2004 |
| JP | 2005-500119 | 1/2005 |
| JP | 2006-516902 | 7/2006 |
| JP | 2006-517112 | 7/2006 |
| JP | 2009-118967 | 6/2009 |
| KR | 10-2005-0072908 | 7/2005 |
| KR | 6013299 | 2/2006 |
| KR | 2006-59142 | 6/2006 |
| NZ | 501224 | 3/2002 |
| NZ | 531262 | 12/2005 |
| RU | 1823791 | 6/1993 |
| RU | 2139690 | 10/1999 |
| RU | 2139734 | 10/1999 |
| RU | 2175855 | 11/2001 |
| RU | 2241389 | 12/2004 |
| RU | 2268752 | 1/2006 |
| SU | 1745214 | 7/1992 |
| SU | 1752358 | 8/1992 |
| WO | 96/06565 | 3/1966 |
| WO | 86/00020 | 1/1986 |
| WO | 87/01270 | 3/1987 |
| WO | 88/09157 | 12/1988 |
| WO | 89/05618 | 6/1989 |
| WO | 90/09149 | 8/1990 |
| WO | 90/14795 | 12/1990 |
| WO | 92/22336 | 12/1992 |
| WO | 95/16399 | 6/1995 |
| WO | 95/29637 | 11/1995 |
| WO | 98/52473 | 11/1998 |
| WO | 98/55031 | 12/1998 |
| WO | 99/21488 | 5/1999 |
| WO | 99/33401 | 7/1999 |
| WO | 99/52478 | 10/1999 |
| WO | 99/59477 | 11/1999 |
| WO | 99/62431 | 12/1999 |
| WO | 00/51658 | 9/2000 |
| WO | 00/51685 | 9/2000 |
| WO | 01/06952 | 2/2001 |
| WO | 01/56626 | 8/2001 |
| WO | 03/001979 | 1/2003 |
| WO | 03/003925 | 1/2003 |
| WO | 03/017850 | 3/2003 |
| WO | 03/045255 | 6/2003 |
| WO | 03/077772 | 9/2003 |
| WO | 03/092758 | 11/2003 |
| WO | 03/103733 | 12/2003 |
| WO | 03/103972 | 12/2003 |
| WO | 03/105703 | 12/2003 |
| WO | 2004/014236 | 2/2004 |
| WO | 2004/030517 | 4/2004 |
| WO | 2004/030520 | 4/2004 |
| WO | 2004/030704 | 4/2004 |
| WO | 2004/030705 | 4/2004 |
| WO | 2004/062459 | 7/2004 |
| WO | 2004/100801 | 11/2004 |

(56) References Cited

FOREIGN PATENT DOCUMENTS

| WO | 2004/112853 | 12/2004 |
|---|---|---|
| WO | 2005/016176 | 2/2005 |
| WO | 2005/074913 | 8/2005 |
| WO | 2005/112787 | 12/2005 |
| WO | 2006/005144 | 1/2006 |
| WO | 2006/061868 | 6/2006 |
| WO | 2006/082060 | 8/2006 |
| WO | 2006/099703 | 9/2006 |
| WO | 2007/053812 | 5/2007 |
| WO | 2007/089864 | 8/2007 |
| WO | 2007/133103 | 11/2007 |
| WO | 2007/145614 | 12/2007 |
| WO | 2008/128113 | 10/2008 |
| WO | 2008/150773 | 12/2008 |
| WO | 2009/042841 | 4/2009 |
| WO | 2009/068252 | 6/2009 |
| WO | 2009/087105 | 7/2009 |
| WO | 2009/097556 | 8/2009 |
| WO | 2009/151876 | 12/2009 |
| WO | 2010/052007 | 5/2010 |
| WO | 2011/139916 | 11/2011 |
| WO | 2011/140283 | 11/2011 |

OTHER PUBLICATIONS

European Search Report re: EP05025816 dated Jun. 23, 2006.
European Search Report for EP07006258.3 dated May 4, 2007, 4 pages.
European Search Report for EP07015906 dated Oct. 2, 2007.
European Search Report for EP07015905.8 dated Oct. 23, 2007, 2 pages.
European Search Report for EP07016222 dated Jan. 7, 2008.
European Search Report for EP10000629.5 dated Mar. 10, 2010, 4 pages.
European Search Report re: EP10000486 dated Apr. 23, 2010.
European Search Report for EP10011871.0 dated Dec. 3, 2010, 2 pages.
European Search Report for EP10011868.6 dated Dec. 6, 2010, 2 pages.
European Search Report for EP10011869 dated Jan. 20, 2011.
European Search Report for EP10186592.1 dated Jan. 19, 2011, 2 pages.
Extended European Search Report re: 07015905.8 dated Oct. 2, 2007.
Extended European Search Report re: 07016222.7 dated Jan. 30, 2008.
International Preliminary Examination Report re: PCT/US1998/10478 dated Dec. 11, 1999.
International Search Report for PCT/US1998/10478 dated Sep. 23, 1998.
International Search Report for PCT/US2002/027525 dated Dec. 9, 2002, 3 pages.
International Search Report for PCT/2003/30666 dated Dec. 15, 2004.
International Search Report for PCT/US2003/25088 dated Dec. 29, 2003.
International Search Report for PCT/US2007/074658 dated Jun. 12, 2007, 3 pages.
International Search Report for PCT/US2008/060127 dated Sep. 23, 2008, 5 pages.
International Search Report for PCT/US2008/0064921 dated Nov. 19, 2008, 3 pages.
International Search Report for PCT/US2008/075849 dated Mar. 18, 2009, 4 pages.
Partial European Search Report re: EP05025816 dated Mar. 20, 2006.
Singapore Search Report for Singapore Patent Application No. 200702625-5 dated Nov. 26, 2008, 7 pages.
Singapore Search Report for Singapore Patent Application No. 200702350-0 dated Nov. 26, 2008, 6 pages.
Singapore Search Report for Singapore Patent Application No. 200703688-2 dated Nov. 26, 2008, 7 pages.
Supplementary European Search Report re: EP98923664 dated Jun. 12, 2001.
Supplementary European Search Report re: EP03785177 dated May 19, 2009.
U.S. Appl. No. 08/859,887, filed May 21, 1997.
U.S. Appl. No. 09/896,455, filed Jun. 29, 2001.
U.S. Appl. No. 09/919,750, filed Jul. 31, 2001.
U.S. Appl. No. 09/943,733, filed Aug. 31, 2001.
U.S. Appl. No. 10/216,516, filed Aug. 9, 2002.
U.S. Appl. No. 10/065,280, filed Sep. 30, 2002.
U.S. Appl. No. 10/065,279, filed Sep. 30, 2002.
U.S. Appl. No. 10/065,278, filed Sep. 30, 2002.
U.S. Appl. No. 10/914,755, filed Aug. 9, 2004.
U.S. Appl. No. 10/941,347, filed Sep. 15, 2004.
U.S. Appl. No. 11/154,230, filed Jun. 16, 2005.
U.S. Appl. No. 11/154,863, filed Jun. 16, 2005.
U.S. Appl. No. 11/307,901, filed Feb. 27, 2006.
U.S. Appl. No. 11/307,900, filed Feb. 27, 2006.
U.S. Appl. No. 11/440,621, filed May 25, 2006.
U.S. Appl. No. 11/440,631, filed May 25, 2006.
U.S. Appl. No. 11/968,494, filed Jan. 2, 2008.
U.S. Appl. No. 11/968,496, filed Jan. 2, 2008.
U.S. Appl. No. 12/119,749, filed May 13, 2008.
U.S. Appl. No. 12/340,530, filed Dec. 19, 2008.
U.S. Appl. No. 12/495,497, filed Jun. 30, 2009.
U.S. Appl. No. 61/357,018, filed Jun. 21, 2010.
U.S. Appl. No. 12/849,960, filed Aug. 4, 2010.
U.S. Appl. No. 12/849,969, filed Aug. 4, 2010.
U.S. Appl. No. 12/849,977, filed Aug. 4, 2010.
U.S. Appl. No. 12/849,983, filed Aug. 4, 2010.
U.S. Appl. No. 12/849,991, filed Aug. 4, 2010.
U.S. Appl. No. 12/850,035, filed Aug. 4, 2010.
U.S. Appl. No. 12/850,063, filed Aug. 4, 2010.
U.S. Appl. No. 13/164,438, filed Jun. 20, 2011.
U.S. Appl. No. 13/335,220, filed Dec. 22, 2011.
US 6,447,535 (withdrawn).
US 6,503,260 (withdrawn).
Bacci, Pier Antonio, "Chirurgia Estetica Mini Invasiva Con Fili Di Sostegno", Collana di Arti, Pensiero e Scienza; Minelli Editore—2006; 54 pgs.
Behl, Marc et al., "Shape-Memory Polymers", Materials Today Apr. 2007; 10(4); 20-28.
Belkas, J. S. et al., "Peripheral nerve regeneration through a synthetic hydrogel nerve tube", Restorative Neurology and Neuroscience 23 (2005) 19-29.
Bellin, I. et al., "Polymeric triple-shape materials", Proceedings of the National Academy of Sciences of the United States of America Nov. 28, 2006; 2103(48):18043-18047.
Boenisch, U.W. et al 'Pull-Out strength and stiffness of meniscal repair using absorbable arrows or Ti-Cron vertical and horizontal loop sutures' American Journal of Sports Medicine, Sep.-Oct. (1999) vol. 27, Issue 5, pp. 626-631.
Buckley, P.R. 'Actuation of Shape Memory Polymer using Magnetic Fields for Applications in Medical Devices' Master of Science in Mechanical Engineering in Massachusetts Institute of Technology Jun. 2003, 144 pages.
Buncke, Jr., H.J. et al 'The Suture Repair of One-Millimeter Vessels, microvascular surgery' (1966) Report of First Conference; Oct. 6-7 pp. 24-35.
Bunnell, S. 'Gig pull-out suture for tendons' J Bone Joint Surg Am (1954) vol. 36A, No. 4 pp. 850-851.
CCPR Centro De Cirurgia Plastica e Reabilitacao Up Lifting (Aptos Threads) http://ccpr.com.br/upl-l.htm, Aug. 19, 2002 pp. 1-2.
Dahlin, Lars, "Techniques of Peripheral Nerve Repair", Scandinavian Journal of Surgery 97: 310-316, 2008.
Datillo, Jr. P.P. et al 'Medical Textiles: Application of an Absorbable Barbed Bi-Directional Surgical Suture' (2002) The Journal of Textile and Apparel Technology and Management vol. 2, Issue 2, pp. 1-5.
Datillo, Jr., P. et al 'Tissue holding performance of knodess absorbable sutures' Society for Biomaterials 29th Annual Meeting Transactions (2003) p. 101.
Declaration of Dr. Gregory L. Ruff, dated Aug. 19, 2005, 8 pages, with Exhibits A-E.

(56) References Cited

OTHER PUBLICATIONS

De Persia, Raúl et al., "Mechanics of Biomaterials: Sutures After the Surgery", Applications of Engineering Mechanics in Medicine, GED-University of Puerto Rico, Mayaguez May 2005, p. F1-F27.
Delorenzi, C.L., "Barbed Sutures: Rationale and Technique", Aesthetic Surg. J. Mar. 26, 2006 (2): 223-229.
Demyttenaere, Sebastian V. et al., "Barbed Suture for Gastrointestinal Closure: a Randomized Control Trial", Surgical Innovation; vol. 16, No. 3; Sep. 2009; pp. 237-242.
Einarsson, Jon I. et al., "Barbed Suture, now in the toolbox of minimally invasive gyn surgery", OBG Management; vol. 21, No. 9; Sep. 2009; pp. 39-41.
Gross, Alex, "Physician perspective on thread lifts", Dermatology Times Feb. 27, 2006(2): 2 pages.
Han, H. et al 'Mating and Piercing Micromechanical Suture for Surface Bonding Applications' (1991) Proceedings of the 1991 Micro Electro Mechanical Systems (MEMS>91), An Investigation of Micro Structures, Sensors, Actuators, Machines and Robots pp. 253-258.
Ingle, N.P. et al 'Barbed Suture Anchoring Strength: Applicability to Dissimilar Polymeric Materials' College of Textiles, North Carolina State University, 7th World Biomaterials Congress 2004, 1 page.
Ingle, N.P. et al 'Mechanical Performance and Finite Element Analysis of Bi-directional Barbed Sutures' Master of Science in Textile Technology & Management at North Carolina State University Aug. 2003, 126 pages.
Ingle, N.P. et al., "Optimizing the tissue anchoring performance of barbed sutures in skin and tendon tissues", Journal of Biomechanics 43 (2010); pp. 302-309.
Ingle, Nilesh P et al., "Testing the Tissue-holding Capacity of Barbed Sutures", College of Textiles, North Carolina State University, Fiber Science, The Next Generation Oct. 17-19, 2005, New Jersey Institute of Technology, Newark, NJ, 4 pages.
Jennings et al 'A New Technique in primary tendon repair' Surg Gynecol Obstet (1952) vol. 95, No. 5 pp. 597-600.
Kaminer, M. et al., "ContourLift™: A New Method of Minimally Invasive Facial Rejuvenation", Cosmetic Dermatology Jan. 2007; 20(1): 29-35.
Kelch et al., "Shape-memory Polymer Networks from Olio[(0-hydroxycaproate)-co-glycolate]dimethacrylates and Butyl Acrylate with Adjustable Hydrolytic Degradation Rate", Biomacromolecules 2007; 8(3):1018-1027.
Khademhosseini, Ali et al., "Nanobiotechnology Drug Delivery and Tissue Engineering", Chemical Engineering Progress 102:38-42 (2006).
Kuniholm J.F. et al 'Automated Knot Tying for Fixation in Minimally Invasive, Robot Assisted Cardiac Surgery' Master of Science in Mechanical & Aerospace Engineering at North Carolina State University May 2003, 71 pages.
Lendelin, A. et al 'Biodegradable, Elastic Shape-Memory Polymers for Potential Biomedical Applications' (2002) Science vol. 296 pp. 1673-1676.
Lendelin, A. et al 'Shape-Memory Polymers' Agnew Chem Int. Ed. (2002) vol. 41 pp. 2034-2057.
Leung, J. et al 'Barbed, Bi-directional Medical Sutures: Biomechanical Properties and Wound Closure Efficacy Study' 2002 Society for Biomaterials 28th Annual Meeting Transactions 1 page.
Leung, J. et al 'Barbed, Bi-directional Surgical Sutures' International Conference & Exhibition on Healthcare & Medical Textiles, Jul. 8-9, 2003 pp. 1-8.
Leung, J. et al 'Barbed, Bi-directional Surgical Sutures: In Vivo Strength and Histopathology Evaluations' 2003 Society for Biomaterials 29th Annual Meeting Transactions pp. 100.
Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.
Leung, J. et al 'Performance Enhancement of a Knotless Suture via Barb Geometry Modifications' 7th World Biomaterials Congress 2004, 1 page.

Li, Y.Y. et al 'Polymer Replicas of Photonic Porous Silicon for Sensing and Drug Delivery Applications' (2003) Science vol. 299 pp. 2045-2047.
Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.
Madduri, Srinivas, et al., "Neurotrophic factors release from nerve conduits for peripheral axonal regeneration", European Cells and Materials vol. 16; Suppl. 1 (2008), p. 14.
Maitland et al., "Prototype laser-activated shape memory polymer foam device for embolic treatment of aneurysms", Journal of Biomedical Optics May/Jun. 2007; 12(3): pp. 030504-1 to 030504-3.
Malina, M. et al 'Endovascular AAA Exclusion: Will Stents with Hooks and Barbs Prevent Stent-Graft Migration' Journal Endovascular Surgery (1998) vol. 5 pp. 310-317.
Mansberger et al 'A New Type Pull-Out Wire for Tendon Surgery: A Preliminary Report' Department of Surgery, University Hospital and University of Maryland School of Medicine, Baltimore, Maryland, Received for Publication May 10, 1951 pp. 119-121.
Mason, M.L. 'Primary and Secondary Tendon Suture. A discussion of the significance of technique in tendon surgery' (1940) Surg Gynecol Obstet 70.
McKee, GK 'Metal anastomosis tubes in tendon suture' The Lancet (1945) pp. 659-660.
McKenzie 'An Experimental Multiple Barbed Suture for the Long Flexor Tendons of the Palm and Fingers' The Journal of Bone and Joint Surgery (1967) vol. 49B, No. 3 pp. 440-447.
Moran et al., "Bidirectional-Barbed Sutured Knotless Running Anastomosis v Classic van Velthovan in a Model System", Journal of Endourology Oct. 2007; 21(10); 1175-1177.
Mullner, "Metal Foam Has a Good Memory", Dec. 18, 2007 Original story at <http://www.physorg.com/news117214996.html>.
Murtha et al., "Evaluation of a Novel Technique for Wound Closure Using a Barbed Suture", Journal of the American Society of Plastic Surgeons 2006; 117(6); 1769-1780.
Nie, Zhihong and Kumacheva, Eugenia, "Patterning surfaces with functional polymers", Nature Materials vol. 7(2008): 277-290.
Paul, Malcolm D. and Rui Avelar, "Quill™ SRS Techniques & Procedures A Novel Approach to Soft Tissue Approximation", Canada, Angiotech Pharmaceuticals, Inc., First Edition 82007: 20 pages.
Paul, Malcolm D. and Rui Avelar, "Quill™ SRS Techniques & Procedures A Novel Approach to Soft Tissue Approximation", Canada, Angiotech Pharmaceuticals, Inc., Fourth Edition 2010, 8 2007-2010: 27 pages.
Paul, Malcolm D. and Rui Avelar, "Quill™ SRS Techniques & Procedures A Novel Approach to Soft Tissue Approximation", Canada, Angiotech Pharmaceuticals, Inc., Second Edition 82008: 20 pages.
Paul, Malcolm D. and Rui Avelar, "Quill™ SRS Techniques & Procedures A Novel Approach to Soft Tissue Approximation", Canada, Angiotech Pharmaceuticals, Inc., Third Edition 2009, 8 2007-2009: 27 pages.
Paul, Malcolm D., "Bidirectional Barbed Sutures for Wound Closure: Evoluation and Applications", Journal of the American College of Certified Wound Specialists (2009) 1, 51-57.
Paul, Malcolm D., "Using Barbed Sutures in Open/Subperiosteal Midface Lifting", Aesthetic Surgery Journal 2006(26): 725-732.
Potenza, A. 'Tendon Healing Within the Flexor Digital Sheath in the Dog: An Experimental Study' Journal of Bone & Joint Surgery (1962) vol. 44A No. 1 pp. 49-64.
Pulvertaft 'Suture Materials and Tendon Junctures' American Journal of Surgery (1965) vol. 109 pp. 346-352.
Quill Medical, Inc. 'Barbed Sutures, wrinkle filters give patients more innovative, non-surgical options' Press Release of Program presented at American Society of Plastic Surgeons annual scientific meeting; Philadelphia, Oct. 9, 2004 3 pages.
Quill Medical, Inc. 'Quill Medical's Novel-Self-Anchoring Surgical Suture Approved for Sale in Europe' Press Release; Research Triangle Park, N.C. May 10, 2004, 1 page.
Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page.
Richert, Ludovic, et al., "Surface Nanopatterning to Control Cell Growth", Advanced Materials 2008(15): 1-5.

(56) References Cited

OTHER PUBLICATIONS

Rodeheaver, G.T. et al., "Barbed Sutures for Wound Closure: In Vivo Wound Security, Tissue Compatibility and Cosmesis Measurements", Society for Biomaterials 30th Annual Meeting Transactions, 2005, 2 pages.
Rofin-Baasel 'Laser Marking on Plastic Materials' (2001) RB50.0, Rofin-Baasel Inc. 2 pages.
Ruff, Gregory, "Technique and Uses for Absorbable Barbed Sutures", Aesthetic Surgery Journal Sep./Oct. 2006; 26:620-628.
Scherman, Peter et al., "Sutures as longitudinal guides for the repair of nerve defects-Influence of suture numbers and reconstruction of nerve bifurcations", Restorative Neurology and Neuroscience 23 (2005) 79-85.
Schmid A. et al 'The outspreading anchor cord. A material for arthroscopic suturing of a fresh anterior cruciate ligament rupture' Surgical Clinic of the University of Gottingen.
Semenov, G.M. et al 'Surgical Suture' (2001) Piter, Saint Petersburg, pp. 12-13 and 92-98.
Serafetinides, AA 'Short pulse laser beam interactions with polymers biocompatible materials and tissue' Proce SPIE vol. 3052 (1996) pp. 111-123.
Sulamanidze, Marlen et al., "APTOS Suture Lifting Methods: 10 Years of Experience", Clin Plastic Surg 36 (2009); pp. 281-306.
Sulamanidze, M.A. et al 'Clinical aspects of bloodless facelift using APTOS filaments' A.V. Vishnevsky Institute of Surgery, Bol=shaya Serpukhovskaya ul, 7, 113811, Moscow, Russia (2002) pp. 24-34.
Sulamanidze, M.A. et al 'Facial lifing with Aptos threads' International Journal of Cosmetic Surgery and Aesthetic Dermatology (2001) No. 4 pp. 1-8.
Sulamanidze, M.A. et al 'Facial lifing with "Aptos" threads' http://fonendo.com (Jul. 18, 2001) pp. 1-4.
Sulamanidze, M.A. et al 'Management of Facial Rhytids by Subcutaneous Soft Tissue Dissection' (2000) International Journal of Cosmetic Surgery and Aesthetic Dermatology vol. 2 No. 4 pp. 255-259.
Sulamanidze, M.A. et al 'Morphological foundations of facelift using APTOS filaments' Bolshaya Serpukhovskaya ul 27, 113811 Moscow, Russia (2002) pp. 19-26.
Sulamanidze, M.A. et al 'Removal of Facial Soft Tissue Ptosis with Special Threads' Dermatol Surg (2002) vol. 28 pp. 367-371.
Sulamanidze, MD, M.A., et al., "Soft tissue lifting in the mid-face: old philosophy, new approach-internal stitching technique (APTOS Needle)", Plastic and Aesthetic Surgery Clinic Total Sharm, Moscow, Russia, (2005):15-29.
Sulzle, Inc. B.G. et al Drilled End Surgical Needles Jul. 2002 Syracuse, New York.
Surgical Specialties Corporation, "Wound Closure Catalog"; Summer 2005, 5 pages.
Szarmach, R. et al 'An Expanded Surgical Suture and Needle Evaluation and Selection Program by a Healthcare Resource Management Group Purchasing Organization' Journal of Long-Term Effects of Medical Implants (2003) vol. 13 No. 3 pp. 155-170.
Tan Ee Lim et al., "A wireless, passive strain sensor based on the harmonic response of magnetically soft materials", Smart Materials and Structures 17 (2008): pp. 1-6.
Up Lifting (Aptos Threads), http.//www.ccpr.com.br/upl-l.htm Aug. 19, 2002 pp. 1-2.
Verdan, C. 'Primary Repair of Flexor Tendons' Journal of Bone and Joint Surgery (1960) vol. 42, No. 4 pp. 647-657.
Villa, Mark T. et al., "Barbed Sutures: A Review of Literature", Plastic and Reconstructive Surgery; Mar. 2008; vol. 121, No. 3; p. 102e-108e.
Wu. W. 'Barbed Sutures in Facial Rejuvenation' Aesthetic Surgery Journal (2004) vol. 24 pp. 582-587.
Zoltan, J. 'Cicatrix Optimia: Techniques for Ideal Wound Healing' English language edition University Park Press Baltimore (1977) Chapter 3 pp. 54-55.
European Search Report for EP09014651 dated Jan. 12, 2010.
European Search Report re: 10004453 dated Jun. 15, 2010.
European Search Report for EP10184766 dated Apr. 20, 2011.
International Preliminary Report re: PCT/US2008/060127 dated Oct. 13, 2009.
International Preliminary Report re: PCT/US2009/040545 dated Oct. 19, 2010.
International Search Report for PCT/US2003/30664 dated May 25, 2004.
International Search Report re: PCT/US2003/030674 dated Sep. 2, 2004.
International Search Report for PCT/US2005/017028 dated Mar. 26, 2008.
International Search Report for PCT/US2011/059238 dated May 21, 2012.
International Search Report for PCT/US2009/040545 dated Oct. 29, 2009.
Supplementary European Search Report re: EP03752630 dated Nov. 17, 2005.
Supplementary European Search Report re: 03754965 dated Nov. 18, 2005.
Supplementary European Search Report re: 05750101 dated Apr. 7, 2010.
Supplementary European Search Report re: 07017663 dated Nov. 7, 2007.
U.S. Appl. No. 10/065,256, filed Sep. 30, 2002.
U.S. Appl. No. 11/691,845, filed Mar. 27, 2007.
U.S. Appl. No. 12/850,397, filed Aug. 4, 2010.
U.S. Appl. No. 12/850,408, filed Aug. 4, 2010.
U.S. Appl. No. 12/850,433, filed Aug. 4, 2010.
U.S. Appl. No. 12/850,447, filed Aug. 4, 2010.
U.S. Appl. No. 12/850,455, filed Aug. 4, 2010.
U.S. Appl. No. 12/850,467, filed Aug. 4, 2010.
U.S. Appl. No. 12/850,480, filed Aug. 4, 2010.
U.S. Appl. No. 12/850,498, filed Aug. 4, 2010.
U.S. Appl. No. 12/972,802, filed Dec. 20, 2010.
Datillo, Jr., P.P. 'Knotless Bi-directional Barbed Absorbable Surgical Suture' Dissertation submitted to the Graduate Faculty of North Carolina State University Textile Management and Technology Nov. 2002, 75 pages.
Encyclopedia of Polymer Science and Engineering, edited by H.F. Mark, et al. Wiley-Interscience, New York, 1989.
Immergut, Edmund H., Grulke, Eric A., Abe, Akihiro; Daniel R. 2005 John Wiley & Sons.
Mark, J.E. ed. Physical Properties of Polymers Handbook. American Institute of Physics Press, Woodbury, N.Y., 1996.
Manual for the Rubber Industry, 2nd ed. Bayer AG, Akron, Ohio, 1993.
Polymer Data Handbook, 1999 by Oxford University Press, Inc.
The Vanderbilt Rubber Handbook, 3d ed. R.T. Vanderbilt Co., Norwalk, Conn., 1990.
European Search Report for EP10011872 dated Apr. 20, 2011.
European Search Report for EP10012437 dated Apr. 28, 2011.
International Preliminary Report re: PCT/US2007/002688 dated Aug. 14, 2008.
International Preliminary Report re: PCT/US2008/087788 dated Jun. 22, 2010.
International Preliminary Report re: PCT/US2009/032693 dated Aug. 3, 2010.
International Preliminary Report re: PCT/US2009/041685 dated Oct. 26, 2010.
International Preliminary Report re: PCT/US2009/044274 dated Nov. 17, 2010.
International Preliminary Report re: PCT/US2011/035431 dated Nov. 6, 2012.
International Preliminary Report re: PCT/US2011/059238 dated May 7, 2013.
International Search Report for PCT/US1994/09631 dated Dec. 9, 1994.
International Search Report for PCT/US2002/20449 dated May 20, 2003.
International Search Report for PCT/US2003/030424 dated Nov. 1, 2004.
International Search Report re: PCT/US2004/014962 dated Feb. 24, 2005.

(56) References Cited

OTHER PUBLICATIONS

International Search Report for PCT/US2007/002688 dated Oct. 22, 2007.
International Search Report for PCT/US2008/077813 dated Mar. 31, 2009.
International Search Report for PCT/US2008/082009 dated Feb. 16, 2010.
International Search Report for PCT/US2009/032693 dated Aug. 26, 2009.
International Search Report for PCT/US2009/034703 dated Sep. 28, 2009.
International Search Report for PCT/US2009/063081 dated Aug. 2, 2010.
International Search Report for PCT/US2009/041685 dated Dec. 22, 2009.
International Search Report for PCT/US2009/044274 dated Jan. 15, 2010.
International Search Report for PCT/US2010/056898 dated Aug. 2, 2011.
International Search Report for PCT/US2010/060889 dated Oct. 11, 2011.
International Search Report for PCT/US2011/034660 dated Feb. 8, 2012.
International Search Report for PCT/US2011/035270 dated Jan. 12, 2012.
International Search Report for PCT/US2011/035271 dated Jan. 12, 2012.
International Search Report re: PCT/US2011/035431 dated Jan. 12, 2012.
International Search Report re: PCT/US2011/040014 dated Feb. 9, 2012.
International Search Report for PCT/US2011/060069 dated May 18, 2012.
International Search Report for PCT/US2012/030441 dated Sep. 27, 2012.
International Search Report for PCT/US2012/041001 dated Sep. 26, 2012.
Singapore Search Report for Singapore Patent Application No. 201103117-6 dated Mar. 8, 2013.
Supplementary European Search Report re: 03770556 dated Nov. 17, 2005.
Written Opinion of the International Searching Authority re: PCT/US2010/056898 dated Jul. 29, 2011.
Written Opinion of the International Searching Authority re: PCT/US2012/041001 dated Aug. 27, 2012.
Gross, R.A. et al 'Biodegradable Polymers for the Environment' Science (2002) vol. 297, Issue 5582 pp. 803.
Martin, D.P. et al 'Medical applications of poly-4-hydroxybutyrate: a strong flexible absorbable biomaterial' Biochemical Engineering Journal vol. 16 (2003) pp. 97-105.
Middleton and Tipton 'Synthetic Biodegradable Polymers as Medical Devices' (1998) Medical Plastics and Biomaterials Magazine, 9 pages.

\* cited by examiner

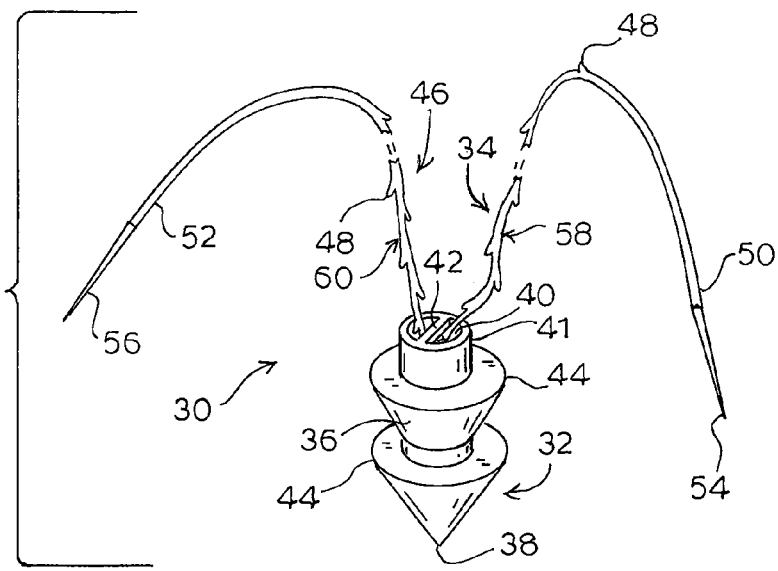

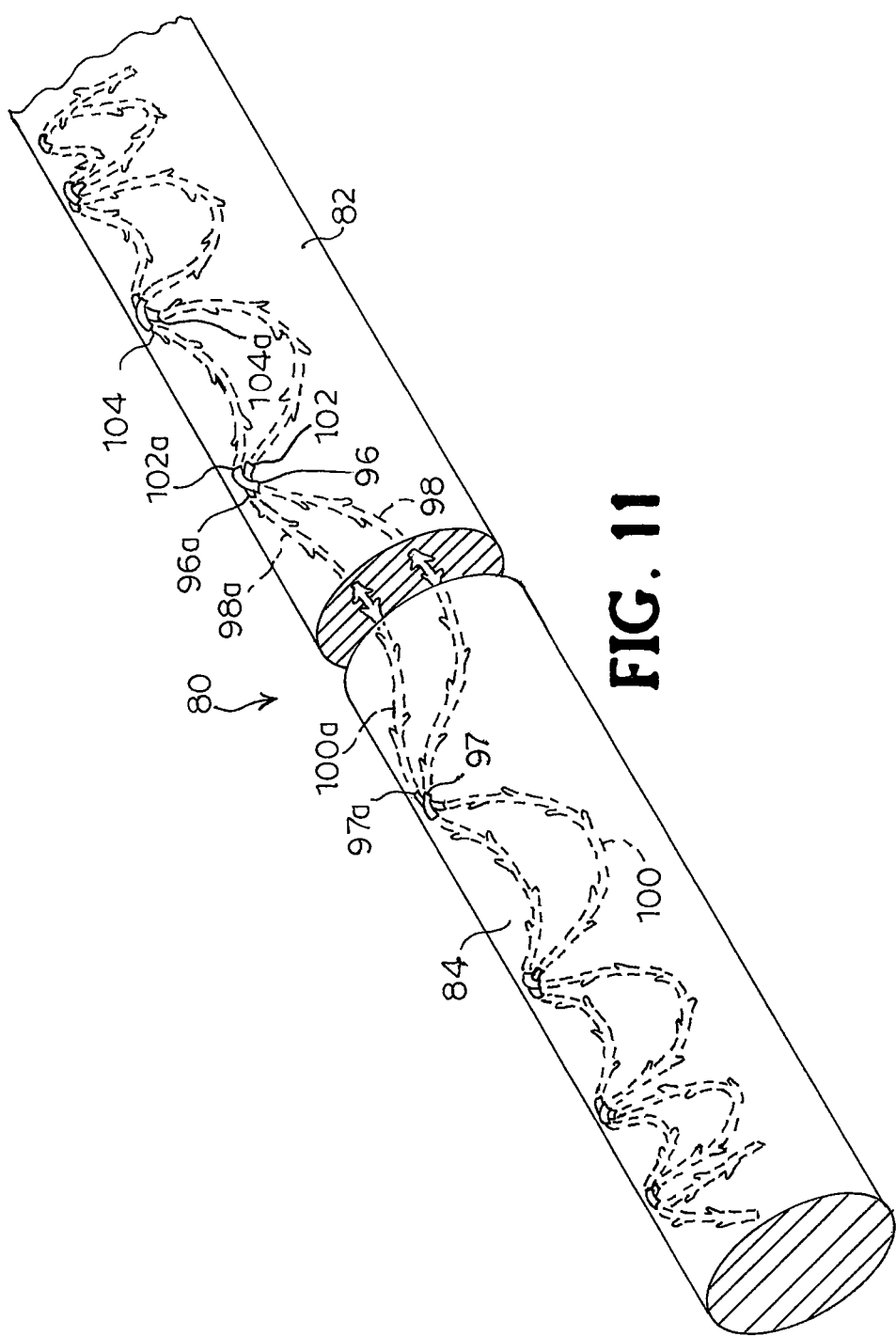

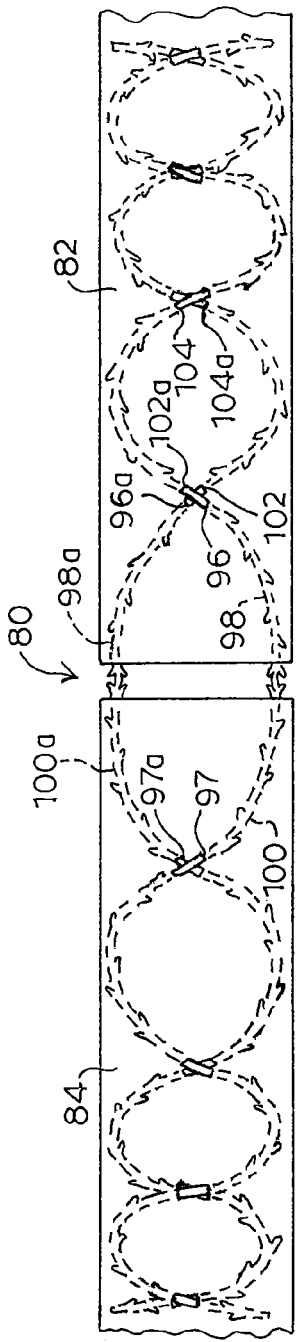
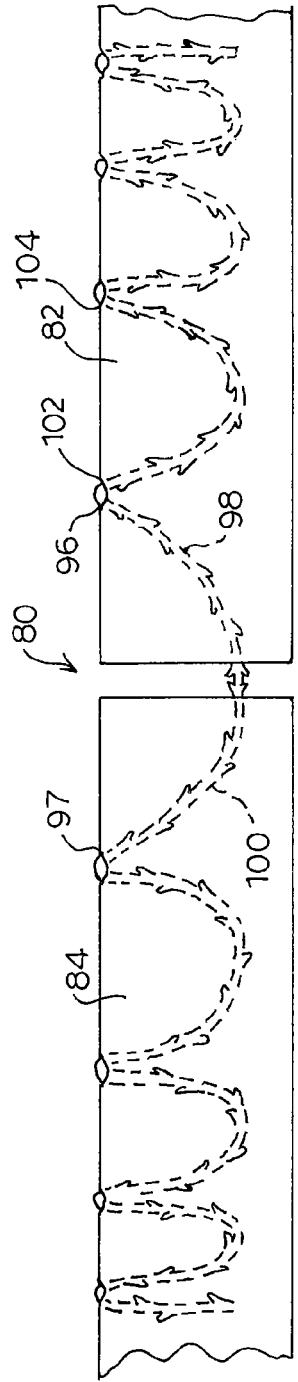

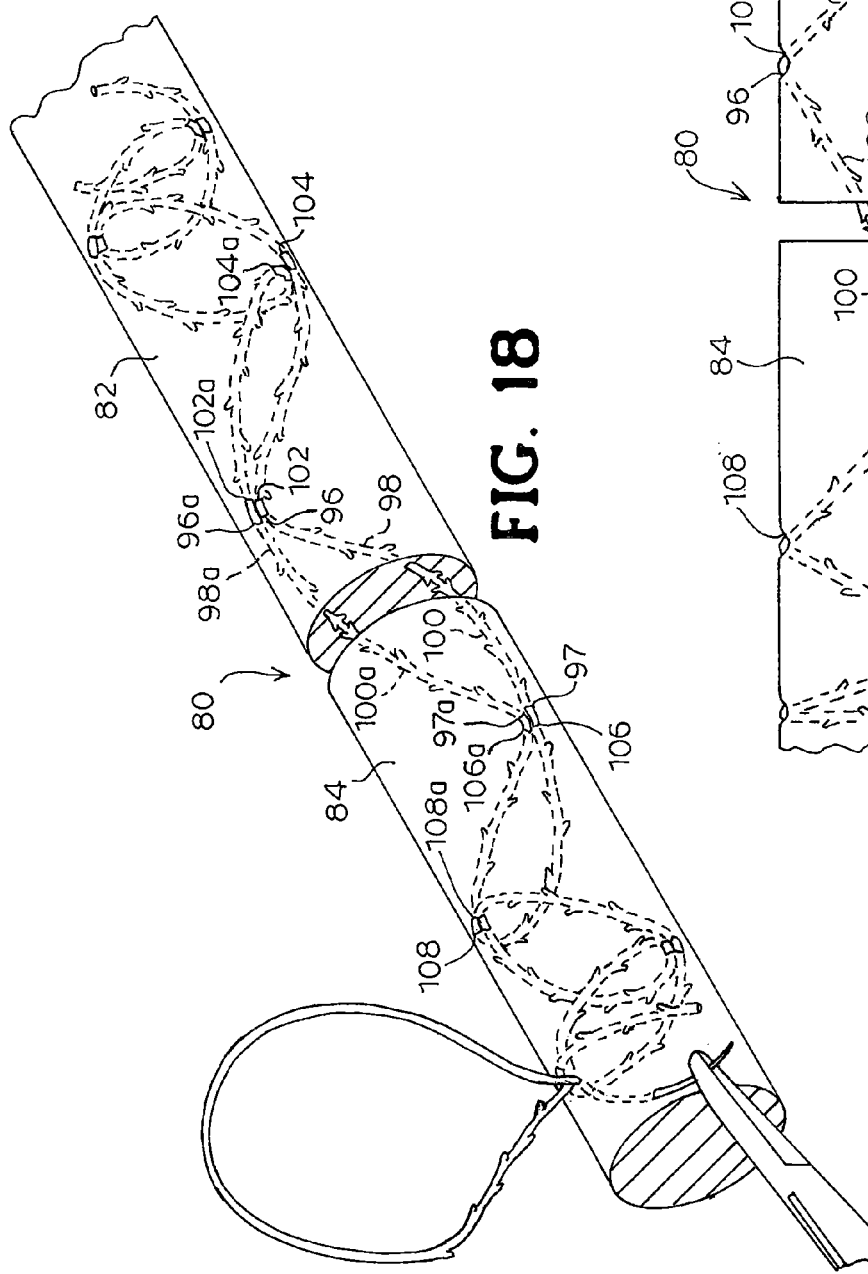
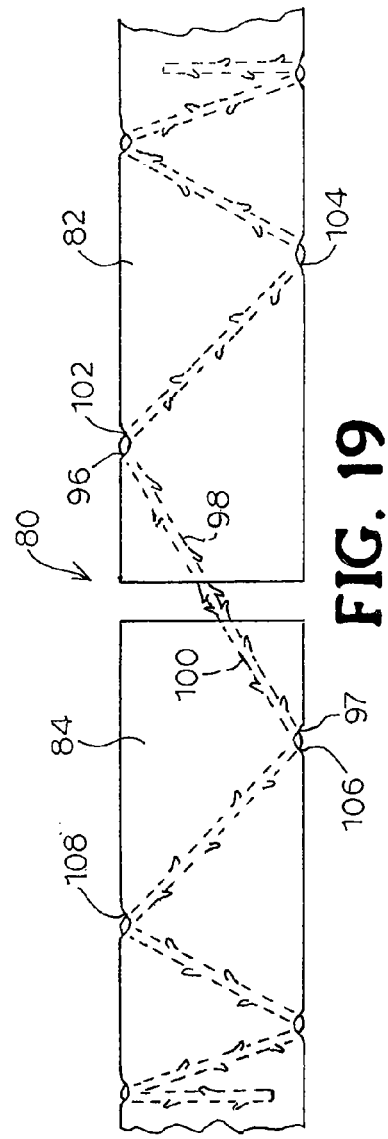
FIG. 18
FIG. 19

MULTIPLE SUTURE THREAD CONFIGURATION WITH AN INTERMEDIATE CONNECTOR

CLAIM TO PRIORITY

This application is a continuation of U.S. application Ser. No. 12/119,749, filed May 13, 2008, now U.S. Pat. No. 8,083,770; which is a divisional of U.S. application Ser. No. 10/914,755, filed Aug. 9, 2004, now U.S. Pat. No. 7,371,253, issued May 13, 2008; which is a divisional of U.S. application Ser. No. 10/216,516, filed Aug. 9, 2002, now U.S. Pat. No. 6,773,450, issued Aug. 10, 2004. All of the above claimed priority applications are incorporated herein by reference in their entireties.

BACKGROUND OF THE INVENTION

This invention relates generally to a device and method for anchoring tissue within a body and, more particularly, to a suture anchor for use in surgical procedures requiring attachment of tissue, such as ligaments, tendons and the like, to other, preferably harder or more fibrous, tissue, such as a bone surface.

Suture anchors are used in surgical procedures wherein it is necessary for a surgeon to attach tissue to the surface of bone, for example, during joint reconstruction and ligament repair or replacement. Suture anchors generally comprise an anchor portion for fixed attachment to the bone, and a suture portion extending from the anchor portion used to connect the tissue to the bone. The anchor portion is often a generally cylindrical body having a sharp pointed end. An impact tool is typically used for driving the pointed end of the anchor into the bone. The outer surface of the anchor portion may be barbed or serrated to prevent the suture anchor from being withdrawn from the bone. The outer surface of the anchor portion could also be threaded and a driver, turned by a conventional drill, used to seat the threaded anchor portion into the bone. The anchor portion may also be fitted into a hole formed in the bone.

With the anchor portion securely in the bone, the suture portion is used for securing the tissue to the bone. The procedure typically involves passing a needle with the suture attached through the tissue. The tissue is advanced along the suture and tension is applied to the suture to draw the tissue tightly against the bone. The needle is removed and the tissue is secured against the bone by knotting the ends of the suture extending from the tissue. The knot is brought down to the surface of the tissue and tightened sufficiently to secure the tissue and bone in close approximation to promote reattachment and healing. A sliding retainer is sometimes used with the suture to pin the tissue against the bone.

There are other conventional suture anchors for attaching tissue to bone. For example, the anchor portion could take other forms including a staple which is driven into the bone surface with the suture positioned between the staple legs and the staple web fixing the suture to the bone surface. Also, a pair of closely-spaced holes can be drilled in the bone for passing the suture into one hole and out the other. However, these procedures are often difficult to perform, particularly in areas with limited access, such as deep wounds.

Further, conventional methods for approximating tissue to bone using a suture are difficult and inefficient because the procedure requires manipulation of the suture for securing the tissue in place. This is a time-consuming part of most surgical procedures, particularly in microsurgery and endoscopic surgery where there is insufficient space to properly manipulate the suture.

For the foregoing reasons, there is a need for an improved suture anchor for use in surgical procedures. The new suture anchor should eliminate the need for tying the suture to hold the tissue against the bone or other tissue surface. The method for using the suture anchor in surgical applications should allow a surgeon to approximate tissue to the bone or tissue surface in an efficient manner. A particularly useful new suture anchor would be used in surgical applications where space is limited such as microsurgery, endoscopic surgery or arthroscopic surgery.

SUMMARY OF THE INVENTION

According to the present invention, a suture anchor is provided for approximating tissue to bone or other tissue. The suture comprises an anchor member adapted to fixedly engage the bone for securing the anchor member relative to the bone. A plurality of sutures are mounted to the proximal end of the anchor member so that the sutures extend outwardly from the anchor member. Each suture has a sharp pointed distal end for penetrating the tissue and a plurality of barbs extending from the periphery of the body. The barbs permit movement of the sutures through the tissue in a direction of movement of the pointed end and prevent movement of the sutures relative to the tissue in a direction opposite the direction of movement of the pointed end.

Also according to the present invention, a method is provided for approximating tissue to a bone or other tissue to allow reapproximation and healing of the tissue and bone in vivo. The method uses a suture anchor including an anchor member adapted to be fixedly mounted to the bone and a plurality of sutures extending from the anchor member. The method comprises the steps of providing on each suture a sharp pointed distal end for penetrating the tissue and a plurality of barbs extending from the periphery of the body. The barbs permit movement of the sutures through the tissue in a direction of movement of the pointed end and prevent movement of the sutures relative to the tissue in a direction opposite the direction of movement of the pointed end. The anchor member is secured in the bone such that the sutures extend from the bone surface and a pointed end of a first suture is inserted into the tissue. The end of the first suture is pushed through the tissue along a curvilinear path in a direction away from the bone until the point at the end of the first suture extends out of the tissue at an exit point in the periphery of the tissue longitudinally spaced from the point of insertion. The pointed end of the first suture is gripped and pulled out of the tissue for drawing the first suture through the tissue while approximating the tissue adjacent the bone along the suture and leaving a length of the first suture in the tissue. The pointed end of the first suture is then inserted into the periphery of the tissue adjacent the exit point and pushed through the tissue along a curvilinear path in the direction away from the bone until the pointed end of the first suture extends out of the tissue at an exit point in the periphery of the tissue longitudinally spaced from the previous insertion point. The pointed end of the first suture is gripped and pulled out of the tissue for drawing the first suture through the tissue leaving a length of the first portion of the suture in the tissue. These steps are repeated with the first suture for advancing longitudinally along the tissue in the direction away from the bone. A second suture is then introduced into the tissue and the previous steps repeated so that the exit and entry points of the second suture are adjacent the corresponding exit and entry points of the first suture and the path of the second suture substantially mirrors the path of the first suture.

BRIEF DESCRIPTION OF THE DRAWINGS

For a more complete understanding of the present invention, reference should now be had to the embodiments shown in the accompanying drawings and described below. In the drawings:

FIG. 1 is a perspective view of an embodiment of a suture anchor according to the present invention;

FIG. 2 is a perspective view of another embodiment of a suture anchor including a plurality of barbed sutures according to the present invention;

FIGS. 11-13 are perspective, side and top plan views, respectively, of the suture pattern generated by the method shown in FIGS. 7-10;

FIGS. 18 and 19 are perspective and side elevation views, respectively, of the suture pattern generated by the method shown in FIGS. 14-17.

DESCRIPTION OF THE PREFERRED EMBODIMENTS

Figure 4:
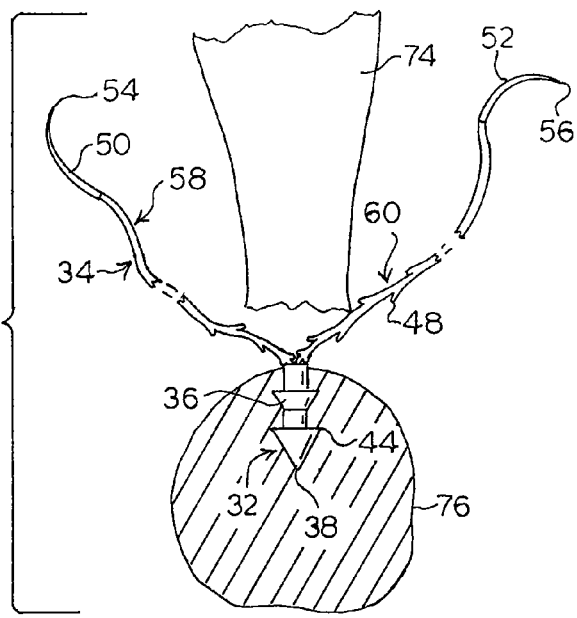
FIGS. 4-6 are schematic views of an embodiment of a method according to the present invention for reattaching the Achilles tendon to bone.

As used herein, the term "tissue" includes tendons, ligaments, cartilage, muscle, skin, organs, and other soft tissue. The term "bone" includes bone, cartilage, tendon, ligament, fascia, and other connective or fibrous tissue suitable for anchor for a suture.

Certain other terminology is used herein for convenience only and is not to be taken as a limitation on the invention. For example, words such as "upper," "lower," "left," "right," "horizontal," "vertical," "upward," and "downward" merely describe the configuration shown in the FIGs. It is understood that the components may be oriented in any direction and the terminology, therefore, should be understood as encompassing such variations unless specified otherwise.

Referring now to the drawings, wherein like reference numerals designate corresponding or similar elements throughout the several views, there is shown in FIG. 1 a suture anchor for use according to the present invention and generally designated at 30. The suture anchor 30 includes an anchor portion 32 and a suture portion 34. The anchor portion 32 comprises an elongated body 36 having a distal pointed tip 38 which serves as a leading end of the suture anchor 30 when the suture anchor is inserted into bone. A blind bore 40, or opening, is formed at the proximal end 41 of the anchor portion 32. A crossbar 42 integral with the anchor body 36 spans the opening 40 for threadably receiving the suture portion 34 at the proximal end of the anchor portion 32.

The anchor portion 32 is shown as having a circular cross-section, although other cross-sectional shapes could be utilized without departing from the present invention. As shown in FIG. 1, ridges 44, or barbs, may be formed on the outer surface of the anchor portion 32 which allow movement of the anchor portion 32 through bone in one direction but which resist the withdrawal of the anchor portion 32 after the anchor portion has been implanted in the bone.

As described above, the anchor portion 32 is driven into the bone surface, pointed tip 38 first, by impact against the proximal end 41, or by turning as when the anchor portion 32 is threaded (not shown). The anchor portion 32 can also be disposed into a hole bored in the bone, in which case insertion can be accomplished with direct pressure or gentle tapping on the proximal end 41 of the anchor portion 32. The ridges 44 on the surface of the anchor body 36 grasp the bone rendering the anchor portion 32 substantially irremovable from the bone. Tension on the suture portion 34 enhances this effect.

The suture portion 34 of the suture anchor 30 has an elongated body 46 and a plurality of barbs 48 disposed along the length of the body 46. First and second ends 50, 52 of the suture body 46 terminate in points 54, 56 for penetrating tissue. The body 46 of the suture portion 34 is, in one embodiment, circular in cross section. Suitable diameters for the body 46 range from about 0.001 mm to about 5.0 mm. The body 46 of the suture portion 34 could also have a non-circular cross-sectional shape which would increase the surface area of the body 46 and facilitate the formation of multiple barbs 48. The length of the suture portion 34 can vary depending on several factors, including the desired surgical application, the type of tissue to be approximated to the bone, the location of the bone, and the like. A suture portion 34 of proper length is selected for achieving suitable results in a particular application.

The plurality of barbs 48 is axially-spaced along the body 46 of the suture portion 34. The barbs 48 are oriented in one direction facing toward the first end 50 of the suture body 46 for a first portion 58 of the length of the suture portion 34 and in an opposite direction facing the second end 52 of the suture body 46 for a second portion 60 of the suture portion 34. The point on the suture body 46 where the barbs 48 change direction is preferably positioned adjacent the crossbar 42 at the proximal end of the anchor body 36. The barbs 48 are yieldable toward the body 46. The barbs 48 on each portion 58, 60 of the suture body 46 are oriented so as to allow movement of the suture portion 34 through the tissue in one direction along with the corresponding end 50, 52 of the suture portion 34. The barbs 48 are generally rigid in an opposite direction to prevent the suture body 46 from moving in the tissue in the opposite direction.

The barbs 48 can be arranged in any suitable pattern, for example, in a helical pattern as shown in FIG. 1. The number, configuration, spacing and surface area of the barbs 48 can vary depending upon the tissue in which the suture portion 34 is used, and depending on the composition and geometry of the suture body 46. The proportions of the barbs 48 may remain relatively constant while the overall length and spacing of the barbs 48 are determined by the tissue being approximated to the bone. For example, if the suture portion 34 is intended to be used in tendon, the barbs 48 can be made relatively short and more rigid to facilitate entry into this rather firm, fibrous tissue. If the suture portion 34 is intended for use in soft tissue, such as fat, the barbs 48 can be made longer and spaced farther apart to increase the holding ability in the soft tissue. Moreover, the ratio of the number of barbs 48 on the first portion 58 of the suture body 46 to the number of barbs 48 on the second portion 60, and the lengths of each portion 58, 60, can vary depending on the surgical application and needs.

The surface area of the barbs 48 can also vary. For example, fuller-tipped barbs 48 can be made of varying sizes designed for specific surgical applications. For joining fat and relatively soft tissues, larger barbs 48 are desired, whereas smaller barbs 48 are more suited for collagen-dense tissues. There are also situations where a combination of large and small barbs 48 within the same structure will be beneficial such as when the suture portion 34 is used in the repair of tissue with differing layered structures. Use of the combination of large and small barbs 48 with the same suture portion 34 wherein barb 48 sizes are customized for each tissue layer will ensure maximum anchoring properties.

The barbs 48 may be formed on the surface of the suture body 46 according to any suitable method, including cutting, molding, and the like. The preferred method is cutting with acute angular cuts directly into the suture body 46 with the cut portions pushed outwardly and separated from the body 46. The depth of the barbs 48 formed in the suture body 46 depends on the diameter of the suture material and the depth of cut. Embodiments of a suitable cutting device for cutting a plurality of axially spaced barbs 48 on the exterior of suture filaments are shown and described in U.S. patent application Ser. No. 09/943,733, entitled "Method Of Forming Barbs On A Suture And Apparatus For Performing Same", which was filed on Aug. 31, 2001, the contents of which are hereby incorporated by reference. This cutting device utilizes a cutting bed, a cutting bed vise, a cutting template, and a blade assembly to perform the cutting. When operated, the cutting device has the ability to produce a plurality of axially spaced barbs 48 in the same or random configuration and at different angles in relation to each other. Various other suitable methods of cutting the barbs 48 have been proposed including the use of a laser. The barbs 48 could also be cut manually. However, manually cutting the barbs 48 is labor intensive, decreases consistency, and is not cost effective. The suture portion 34 could also be formed by injection molding, extrusion, stamping and the like.

Barbed sutures suitable for use according to the methods of the present invention are described in U.S. Pat. No. 5,342,376, entitled "Inserting Device for a Barbed Tissue Connector", U.S. Pat. No. 6,241,747, entitled "Barbed Bodily Tissue Connector", and U.S. Pat. No. 5,931,855. The contents of U.S. Pat. No. 5,342,376, U.S. Pat. No. 5,931,855 and U.S. Pat. No. 6,241,747 are hereby incorporated by reference.

The suture portion 34 is attached to the proximal end of the anchor portion 32. As seen in FIG. 1, the suture portion 34 is threaded around the crossbar 42 on the anchor body 36. It is understood that the suture portion 34 may be attached to the anchor portion 32 in a number of ways, including inserting the end of the suture body 46 into the bore 40 formed in the proximal end of the anchor body 36 and securing the suture body 46 in place with a set screw, rivet, or the like, or, wherein the material of the anchor portion 32 is metal, by swaging or crimping. The anchor portion 32 and suture portion 34 could also be formed in one piece in the manufacturing process. However, the preferred attachment of the suture portion 34 is as shown in FIG. 1 since this arrangement allows a simple, secure threading of a double-ended suture portion 34 during manufacture or prior to use. Moreover, as seen in FIG. 2, the user may selectively attach several suture portions 34 to the anchor portion 32 depending upon the surgical application.

Suitable material for the body 46 of the suture portion 34 is available in a wide variety of monofilament suture material. The particular suture material chosen depends on strength and flexibility requirements. In one embodiment, the material for the suture body 46 is flexible and substantially nonresilient so that the shape of an inserted suture portion 34 will be determined by the path of insertion and the surrounding tissue. In some applications, however, it may be desirable for at least a portion of the suture body 46 to have sufficient dimensional stability to assume a substantially rigid configuration during use and sufficient resiliency to return to a predetermined position after deflection therefrom. The portions of the ends 50, 52 of the suture body 46 adjacent the points 54, 56 may be formed of a material sufficiently stiff to enable the points 54, 56 to penetrate tissue in which the suture portion 34 is used when a substantially axial force is applied to the body 46. Variations in surface texture of the suture body 46 can impart different interaction characteristics with the tissue.

The ends 50, 52 of the suture portion 34 may be straight (FIG. 1) or curved (FIG. 2). In one embodiment, the ends 50, 52 of the suture portion 34 may be surgical needles secured at each end of the suture portion 34 so that the body 46 extends between the shank ends of the two needles. The needles are preferably constructed of stainless steel or other surgical-grade metal alloy. The needles may be secured to the suture body 46 by means of adhesives, crimping, swaging, or the like, or the joint may be formed by heat shrinkable tubing. A detachable connection may also be employed such that the needles may be removed from the suture body 46 by a sharp tug or pull or by cutting. The length of the needles is selected to serve the type of tissue being repaired so that the needles can be completely removed leaving the suture body 46 in the desired position within the tissue.

The suture anchor 30 of the present invention can be formed of a bioabsorbable material which allows the suture anchor 30 to be absorbed by the body over time. Bioabsorbable material is particularly useful in arthroscopic surgery and procedures. Many compositions useful as bioabsorbable materials can be used to make the suture anchor 30. Generally, bioabsorbable materials are thermoplastic polymers. Selection of the particular material is determined by the desired absorption or degradation time period which depends upon the anticipated healing time for the subject of the procedure. Biodegradable polymers and co-polymers range in degradation time from about one month to over twenty-four months. They include, but are not limited to, polydioxanone, polylactide, polyglycolide, polycaprolactone, and copolymers thereof. Other copolymers with trimethylene carbonate can also be used. Examples are PDS II (polydioxanone), Maxon (copolymer of 67% glycolide and 33% trimethylene carbonate), and Monocryl (copolymer of 75% glycolide and 25% caprolactone). Germicides can also be incorporated into the suture anchor 30 to provide long lasting germicidal properties.

Alternatively, either the anchor portion 32 or the suture portion 34 of the suture anchor 30 can be formed from nonabsorbable material such as, for example, nylon, polyethylene terephthalate (polyester), polypropylene, and expanded polytetrafluoroethylene (ePTFE). The suture body 46 can also be formed of metal (e.g. steel), metal alloys, or the like. Titanium is a preferred material when the anchor portion 32 is to remain permanently in the bone. A suitable anchor portion 32 for use according to the present invention is available from Mitek Products of Norwood, Mass. Alternatively, the anchor portion 32 can also be a rigid barbed structure made from thick monofilament suture material with barbs suitable for anchoring in bone.

In use in an orthopedic surgical procedure, the anchor portion 32 of the suture anchor 30 of the present invention is inserted into bone. Once the anchor portion 32 is fixed in place, the suture portion 34 extends outwardly from the anchor portion 32 and the bone for surgical suturing to tissue to be approximated to the bone. The tissue is brought into position over the suture anchor 30 site. The point 54 at one end 50 of the suture portion 34 is inserted into the tissue such that the point 54 pierces the tissue and the barbs 48 on the portion 58 of the suture body 46 corresponding to the one end 50 yield toward the body 46 to facilitate movement of the suture body as it is drawn through the tissue in the direction of insertion. The point 56 at the other end 52 of the suture portion 34 is also inserted into the tissue and advanced through the tissue in like manner. The tissue is then advanced along the suture portions 58, 60 within the tissue to close the gap between the tissue and the bone. The barbs 48 of the suture body 46 grasp the surrounding tissue and maintain the tissue in position adjacent to the bone during healing. The leading ends 50, 52 of the suture body 46 protruding from the tissue are then cut and discarded.

According to the present invention, a surgical procedure using the suture anchor 30 is provided for approximating a torn Achilles tendon to bone for reattachment and healing. It is understood that the applicants do not intend to limit the suture anchor 30 and method of the present invention to only the reattachment of the Achilles tendon.

Figure 3:
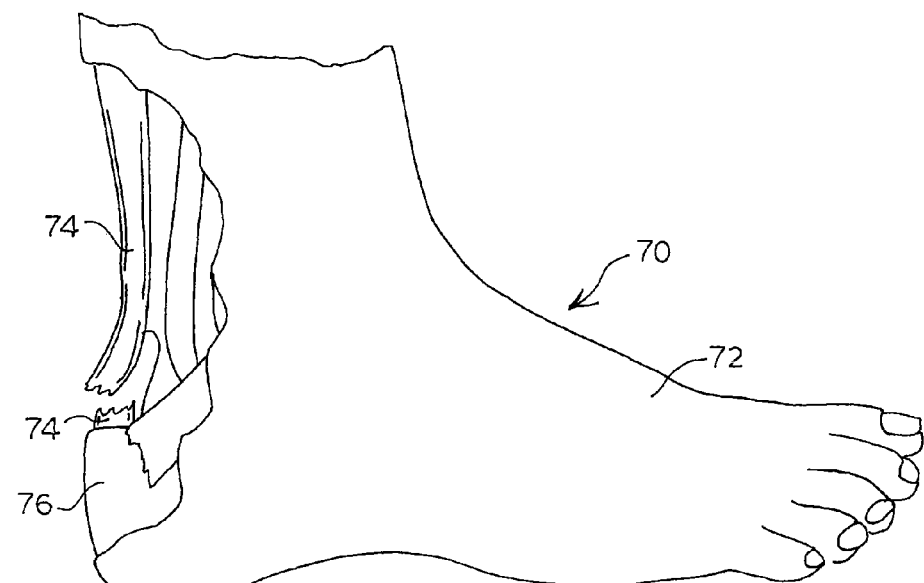
FIG. 3 is a side elevation view of an ankle with a portion of the outer layer of tissue cut-away to schematically show a torn Achilles tendon.
Figure 5:
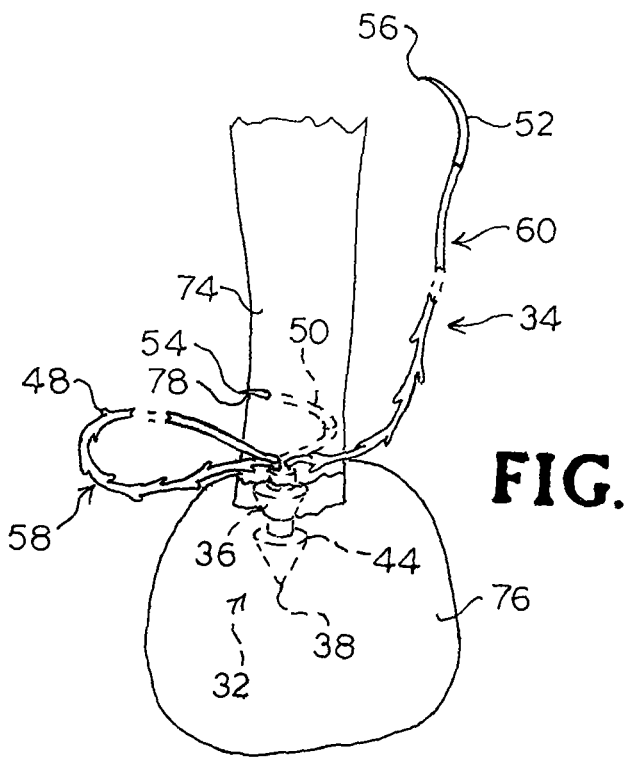
Figure 6:
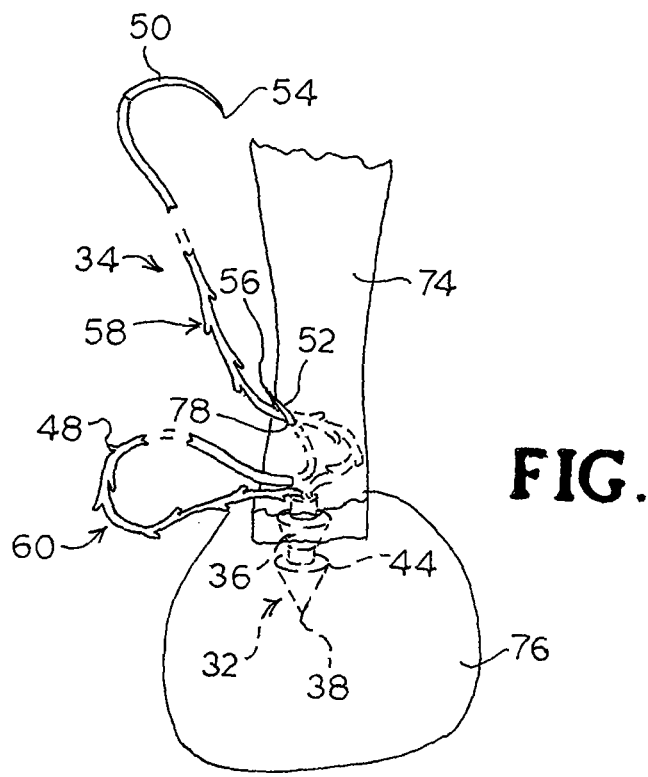

Referring to FIG. 3, a human foot 70 is shown with a portion of the outer layer 72 of skin and tissue cutaway to schematically show the Achilles tendon 74 torn away from the heel bone 76. In this embodiment of the present invention, the user, such as a surgeon, selects a suture anchor 30 (FIG. 4) having a suture portion 34 of sufficient length and having curved ends 50, 52 which, in one embodiment, as noted above may be surgical needles. As seen in FIG. 4, the surgeon begins by inserting the suture anchor 30 into the heel bone 76. The first and second portions 58, 60 of the elongated suture portion 34 extend from the anchor portion 32. Next the surgeon inserts the first end 50 (FIG. 5), or surgical needle, into the free end of the Achilles tendon 74 and pushes the needle 50 through the tendon 74 along a selected curvilinear path until the point 54 at the first end of the needle 50 extends from an exit point 78 at the periphery of the tendon 74 longitudinally spaced from the end of the tendon. The surgeon grips the needle 50 and pulls the needle out of the tendon 74 for drawing the first portion 58 of the suture body 46 through the tendon 74 leaving a length of the first portion 58 of the suture body 46 in the tendon 74 between the end of the tendon and the exit point 78, as seen in FIG. 6. These steps are repeated with the second portion 60 of the suture body 46 beginning with insertion into the end of the tendon 74.

Figure 7:
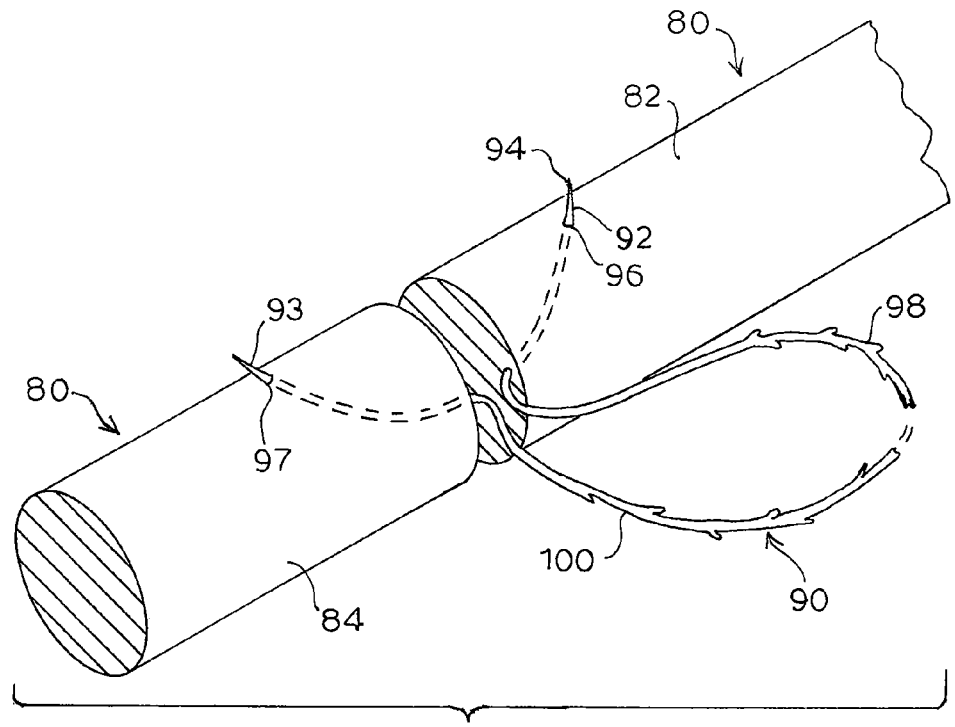
FIGS. 7-10 are perspective views of a method for joining two ends of a severed tendon according to the present invention.
Figure 8:
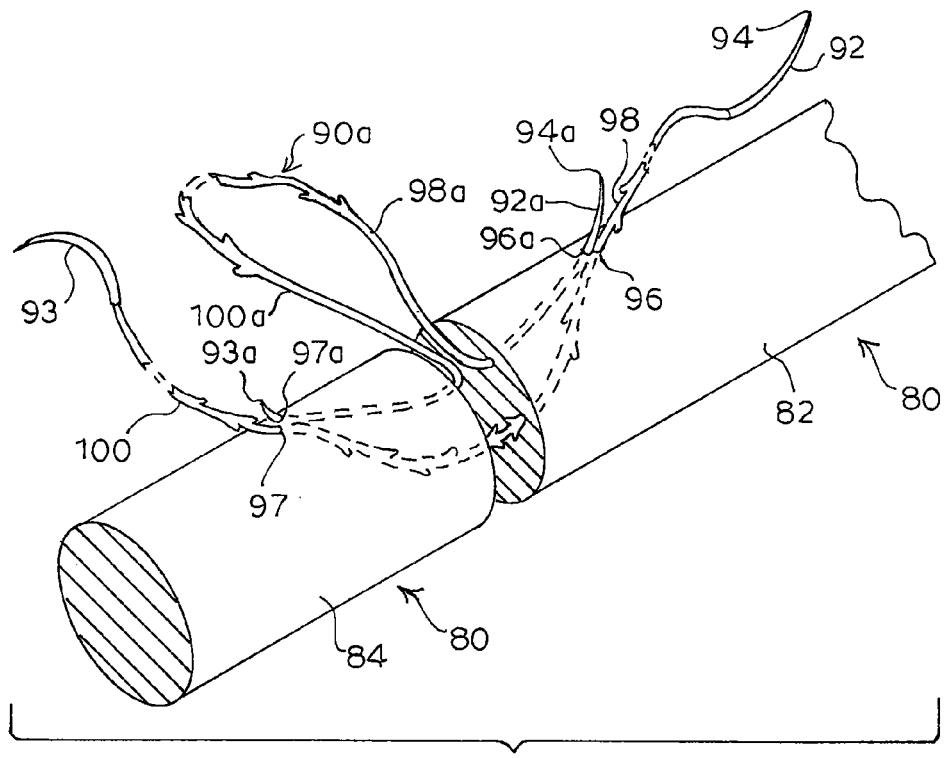

Methods according to the present invention useful in binding together partially or completely severed tendons, or other internal tissue repairs requiring considerable tensile strength, are suitable for use in attaching tissue to bone. One such method for joining two ends 82, 84 of a tendon 80 is shown in FIGS. 7-10. Referring to FIG. 7, the surgeon begins by inserting a first end 92 of a two-way barbed suture 90, which may comprise a straight or curved surgical needle, into one end 82 of the tendon 80 and pushing the needle 92 through the tendon 80 along a selected curvilinear path until the point 94 of the needle 92 extends from an exit point 96 in the periphery of the tendon 80 longitudinally spaced from the one end 82 of the tendon 80. The first needle 92 is gripped and pulled out of the tendon 80 for drawing a first portion 98 of the suture 90 through the tendon 80 leaving a length of the first portion 98 of the suture 90 in the tendon end 82 between the end of the tendon 80 and the exit point 96. As seen in FIG. 7, these steps are repeated with a second portion 100 of the suture 90 at the other end 84 of the tendon 80, wherein a second end 93 of the suture 90 is inserted into the tendon end 84 and advanced along a selected curvilinear path to an exit point 97 longitudinally spaced from the end 84 of the tendon 80. The second end 93 of the suture 90 projecting from the exit point 97 is gripped and pulled out of the tendon 80 for drawing the second portion 100 of the suture 90 through the tendon 80 and leaving a length of the second portion 100 of the suture 90 in the tendon end 84 (FIG. 8).

Referring now to FIG. 8, a second suture 90a is introduced into the ends 82, 84 of the tendon 80. The first needle 92a of the second suture 90a is inserted into the one end 82 of the tendon 80 and pushed through the tendon along a selected curvilinear path until the needle 92a extends from an exit point 96a in the periphery of the tendon 82 substantially co-located with the first exit point 96 of the first portion 98 of the first suture 90. These steps are repeated with the second portion 100a of the second suture 90a at the other end 84 of the tendon 80 such that the exit point 97a in the periphery of the end of the tendon 84 is substantially co-located with the first exit point 97 of the second portion 100 of the first suture 90. The needles 92a, 93a of the second suture 90a are pulled out of the tendon 80 for drawing the first and second portions 98a, 100a, respectively, of the second suture 90a through the tendon 80 leaving a length of the second suture 90a in the tendon 80 between the exit points 96a, 97a.

Figure 9:
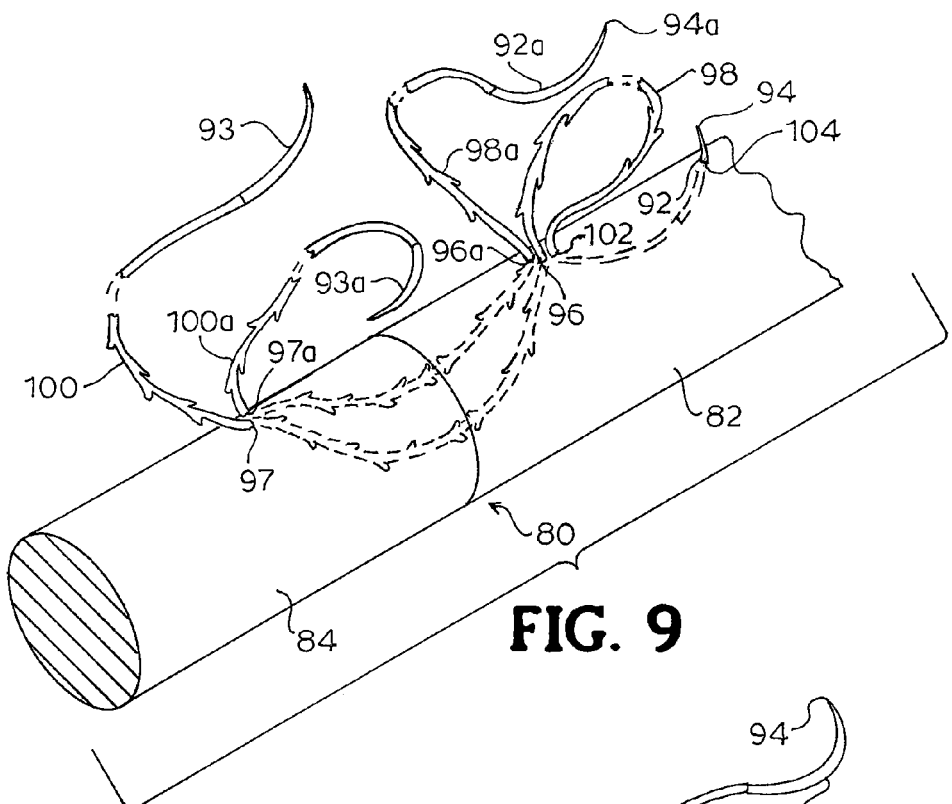
Figure 10:
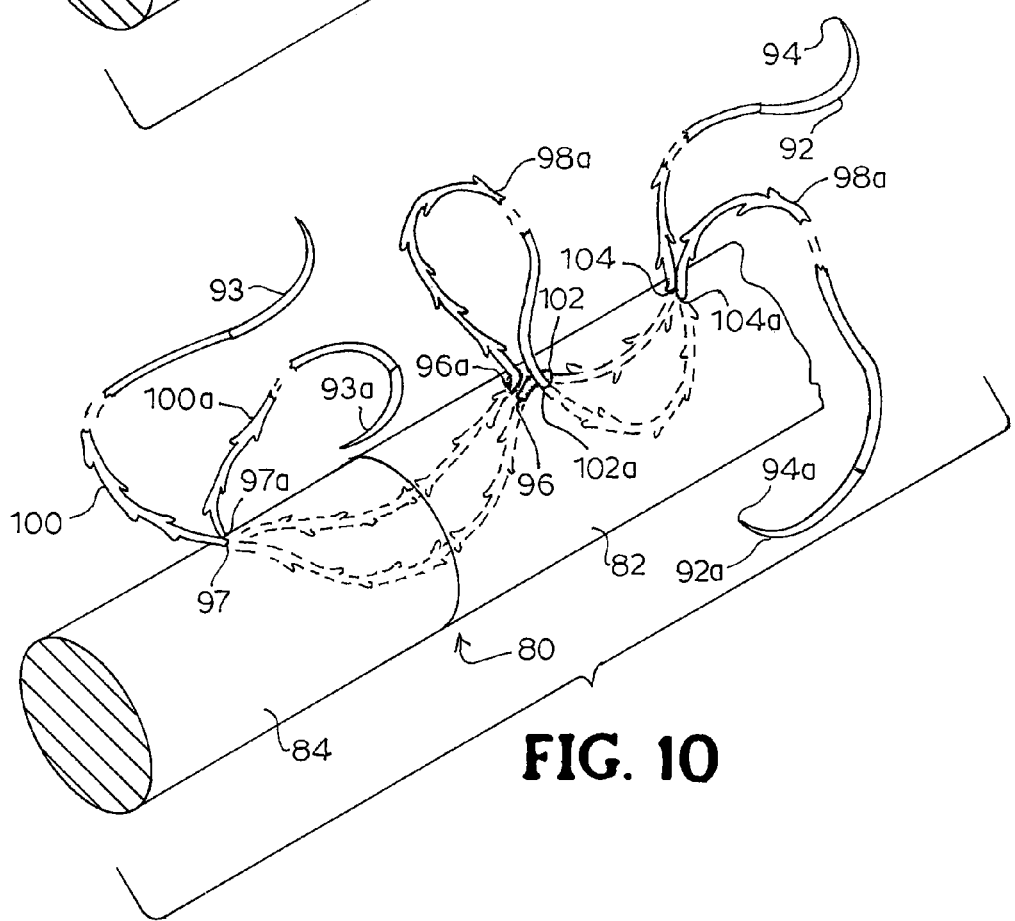

As shown in FIG. 9, the surgeon reinserts the first needle 92 of the first suture 90 into the periphery of the one end 82 of the tendon 80 at an entry point 102 immediately adjacent the exit point 96 and pushes the needle 92 along a selected curvilinear path until the point 94 of the needle 92 exits the same side of the tendon 82 at an exit point 104 that is longitudinally spaced from the entry point 102. It is understood that the surgeon could use the exit point 96 as the entry point 102 for the needle 92 if desired. The surgeon pulls the needle 92 out of the tendon 82 for drawing the first portion 98 of the suture 90 through the tendon 82. The surgeon may then reinsert the needle 92 into the tendon 82 at an entry point (not shown) immediately adjacent the exit point 104 and push the needle 92 along a selected curvilinear path and out of the same side of the tendon 82 at an exit point (not shown) longitudinally spaced from the previous entry point. It is understood that the surgeon makes as many passes as deemed necessary in a "wave-like" pattern for holding the end 82 of the tendon, or as the length or thickness of the tendon 82 allows, and removes the remaining length of the first portion 98 of the suture 90.

The surgeon repeats the steps described above with the first portion 98a of the second suture 90a (FIG. 10) by reinserting the needle 92a into the tendon 82 at an entry point 102a adjacent the exit point 96a, crossing over the first portion 98 of the first suture 90, and pushing the needle 92a along a selected curvilinear path until the needle 92a emerges from an exit point 104a in the periphery of the tendon 82 substantially co-located with the second exit point 104 of the first portion 98 of the first suture 90. In this manner, the surgeon advances longitudinally along the end 82 of the tendon 80 with the first portion 98a of the second suture 90a in a "wave-like" pattern which generally mirrors that of the first portion 98 of the first suture 90.

The previous steps are repeated at the other end 84 of the tendon 80 with the second portions 100, 100a of the first suture 90 and second suture 90a. The pattern of the second portions 100, 100a of the sutures 90, 90a in the second end 84 of the tendon 80 generally mirrors that of the first portions 98, 98a of the sutures in the first end 82 of the tendon 80. Thus, the exit points and entry points of the first and second sutures 90, 90a are substantially co-located.

The ends 82, 84 of the tendon 80 are brought together by pushing the tendon ends along the sutures while maintaining tension on the free ends 92, 92a, 93, 93a of the sutures 90, 90a. The barbs 48 maintain the sutures 90, 90a in place and resist movement of the tendon ends 82, 84 away from this position. The needles along with remaining lengths of the suture portions 98, 98a, 100, 100a are cut and discarded.

FIGS. 11-13 show the suture pattern resulting from use of the above-described method of the present invention. It is understood that we do not intend to limit ourselves to the depth or length of the suture paths shown in the FIGs. as the amount of tissue grasped by each pass, which is related to the depth of the suture path into the tissue and the length of the pass from entry point to exit point, may be determined by the surgeon based on a number of factors including the tissue to be joined.

Figure 14:
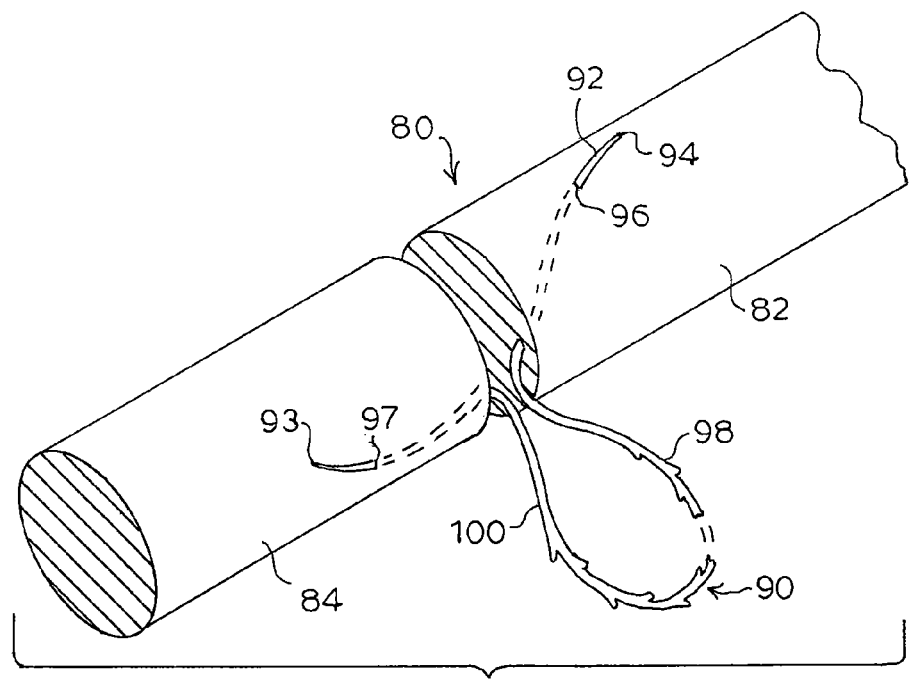
FIGS. 14-17 are perspective views of another method for joining two ends of a severed tendon according to the present invention.
Figure 15:
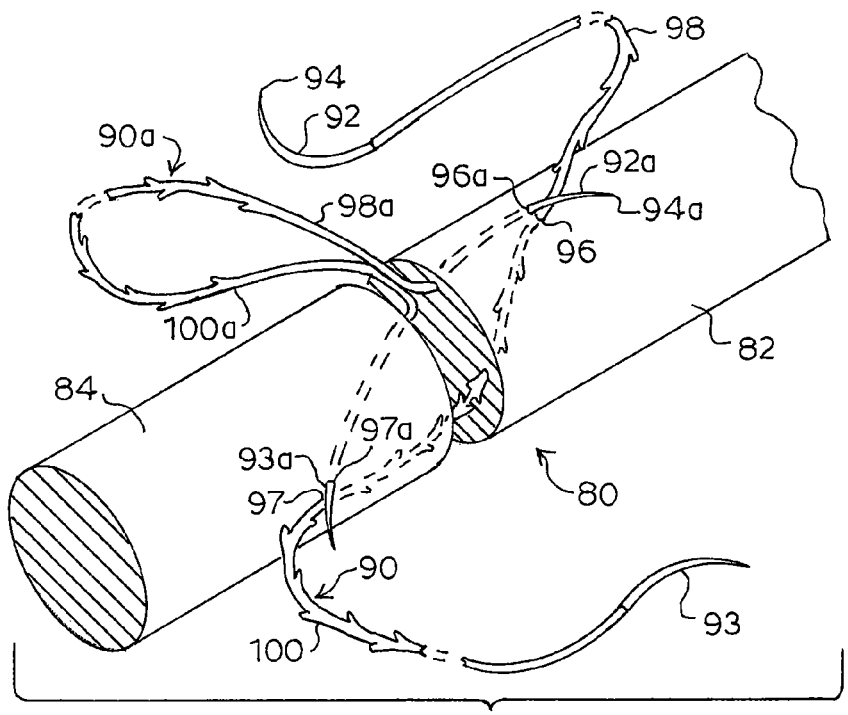

Another method according to the present invention for joining two ends 82, 84 of a tendon 80 which is suitable for use in attaching tissue to bone is shown in FIGS. 14-17. Referring to FIG. 14, the surgeon begins by inserting the first end 92 of a two-way barbed suture 90, which may comprise a straight or curved surgical needle, into one end 82 of the tendon 80 and pushing the needle 92 through the tendon 82 along a selected curvilinear path until the point 94 of the needle 92 extends from an exit point 96 in the periphery of the tendon 82 longitudinally spaced from the one end 82 of the tendon. The first needle 92 is gripped and pulled out of the tendon 82 for drawing the first portion 98 of the suture 90 through the tendon 80 leaving a length of the first portion 98 of the suture in the tendon 80 between the tendon end 82 and the exit point 96. As seen in FIG. 14, these steps are repeated with the second portion 100 of the suture 90 at the other end 84 of the tendon 80. That is, a second end 93 of the suture 90 is inserted into the tendon end 84 and advanced along a selected curvilinear path to an exit point 97 longitudinally spaced from the end 84 of the tendon 80. The exit point 97 of the second needle 93 is on the opposite side of the tendon 80 from the first exit point 96 of the first portion 98 of the suture 90. The second end 93 of the suture 90 projecting from the exit point 97 is gripped and pulled out of the tendon 80 for drawing the second portion 100 of the suture 90 through the tendon 80 and leaving a length of the second portion 100 of the suture 90 in the tendon end 84 (FIG. 15).

Referring now to FIG. 15, a second suture 90a is introduced into the ends 82, 84 of the tendon 80. The first needle 92a of the second suture 90a is inserted into the end 82 of the tendon 80 and pushed through the tendon along a selected curvilinear path until the needle 92a extends from an exit point 96a in the periphery of the tendon 82 substantially co-located with the first exit point 96 of the first portion 98 of the first suture 90. These steps are repeated with the second portion 100a of the second suture 90a at the other end 84 of the tendon 80 such that the exit point 97a in the periphery of the end of the tendon 84 is substantially co-located with the first exit point 97 of the second portion 100 of the first suture 90. The needles 92a, 93a of the second suture 90a are pulled out of the tendon 80 for drawing the first portion 98a and second portion 100a of the second suture 90a through the tendon 80 leaving a length of the second suture 90a in the tendon 80 between the exit points 96a, 97a.

Figure 16:
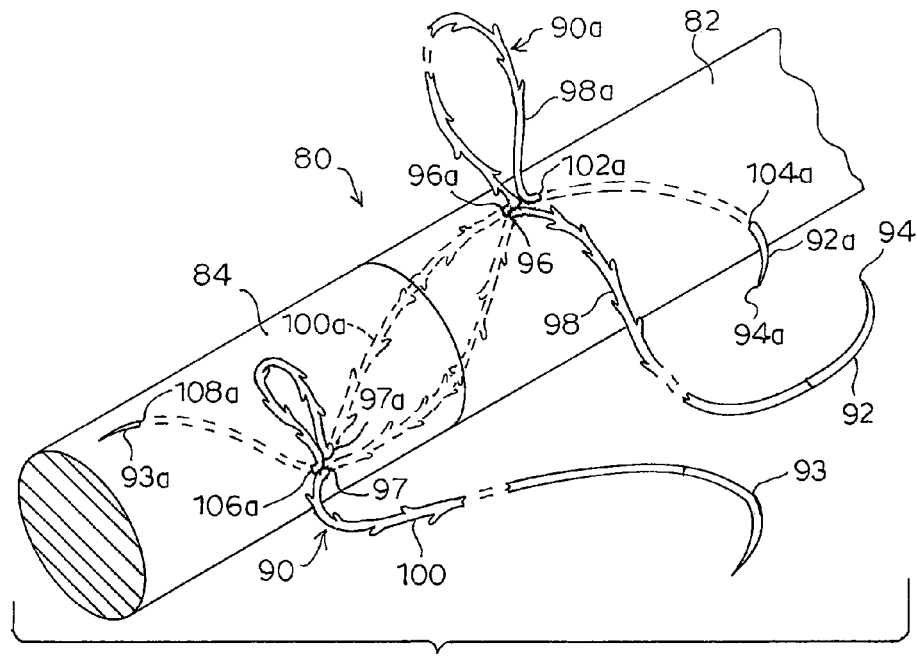
Figure 17:
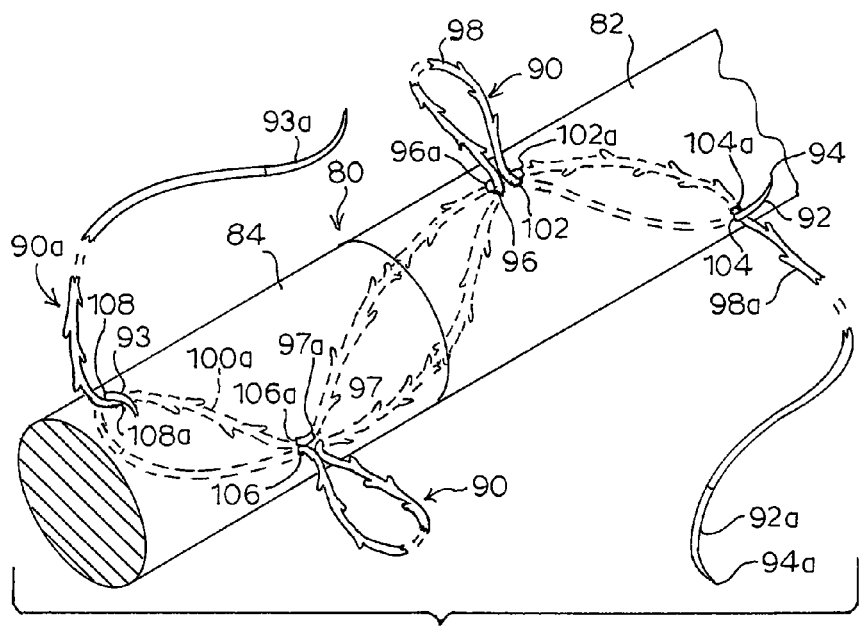

As shown in FIG. 16, the surgeon reinserts the second needle 92a into the periphery of the one end 82 of the tendon 80 at an entry point 102a immediately adjacent the exit point 96a and pushes the needle 92a along a selected curvilinear path until the point 94a of the needle 92a exits the opposite side of the tendon 82 at an exit point 104a that is longitudinally spaced from the entry point 102a. It is understood that the surgeon could use the first exit point 96a as the entry point 102a for the needle 92a if desired. The surgeon pulls the needle 92a out of the tendon 82 for drawing the first portion 98a of the suture 90a through the tendon 82. The surgeon may then reinsert the needle 92a into the tendon 82 at an entry point (not shown) immediately adjacent the exit point 104a and push the needle 92a along a selected curvilinear path and out of the opposite side of the tendon 82 at an exit point (not shown) longitudinally spaced from the previous entry point. It is understood that the surgeon makes as many passes in a "side-to-side" pattern as deemed necessary for holding the end 82 of the tendon 80, or as the length or thickness of the tendon end 82 allows, and removes the remaining length of the first portion 98a of the second suture 90a. With each pass, the longitudinal distance between the entry point and exit point decreases. The surgeon repeats these steps with the second portion 100a of the second suture 90a at the other 84 of the tendon 80. The second end 93a of the suture 90a is inserted into the other end 84 of the tendon 80 at an entry point 106a immediately adjacent the first exit point 97a and advanced along a selected curvilinear path to an exit point 108a opposite and longitudinally spaced from the entry point 106a. The second portion 100a of the second suture 90a is drawn through the tendon 80 leaving a length of the second portion 100a of the suture 90a in the tendon (FIG. 17).

The surgeon repeats the steps described above with the first portion 98 and second portion 100 of the first suture 90 at the ends 82, 84 of the tendon 80. As seen in FIG. 17, the needle 92 at the end of the first portion 98 is inserted into the tendon end 82 at an entry point 102 adjacent the exit point 96 and pushed along a selected curvilinear path until the needle 92 emerges from an exit point 104 in the periphery of the tendon 82 substantially co-located with the second exit point 104a of the first portion 98a of the second suture 90a. In this manner, the surgeon advances longitudinally along the end 82 of the tendon 80 with the first portion 98 of the first suture 90 in a "side-to-side" pattern which generally mirrors that of the first portion 98a of the second suture 90a. Similar steps are taken with the second portion 100 of the first suture 90 in the other end 84 of the tendon 80. The pattern of the first suture 90 and second suture 90a, as well as the respective first portions 98, 98a and second portions 100, 100a of the sutures 90, 90a, generally mirror one another. The exit points and entry points of the sutures are substantially co-located. The ends 82, 84 of the tendon 80 are brought together by pushing the tendon ends along the sutures while maintaining tension on the free ends of the sutures 90, 90a. The barbs 48 maintain the sutures 90, 90a in place and resist movement of the tendon ends 82, 84 away from this position. The needles, along with remaining lengths of the sutures, are cut and discarded. FIGS. 18 and 19 show the suture pattern using the above-described method of the present invention.

It is understood that more sutures may be used in any of the methods of the present invention. The number of sutures used depends on the size, caliber, and length of the tendon to be repaired. Large tendons will require more than two sutures whereas one may suffice for very small tendons. Tendon repair with two sutures according to the present invention exhibits equivalent or better holding power than conventional techniques. Moreover, tendons repaired according to the methods of the present invention maintain their original configuration, profile, contour, and form better when subject to stretching forces. Other methods of tendon repair suitable for use according to the present invention are shown and described in U.S. patent application Ser. No. 09/896,455, entitled "Suture Method", which was filed on Jun. 29, 2001, the contents of which are hereby incorporated by reference.

Figure 21:
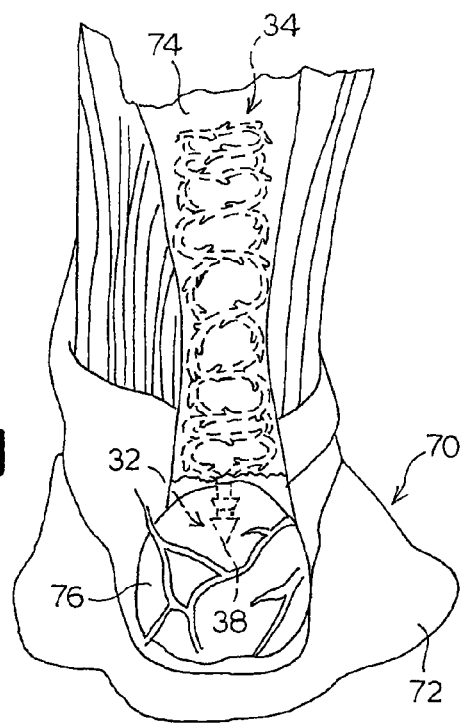
FIGS. 20 and 21 are side and rear elevation views, respectively, of the ankle shown in FIG. 3 with the torn Achilles tendon reattached to the bone using the suture anchor and method shown in FIGS. 7-13 according to the present invention.
Figure 20:
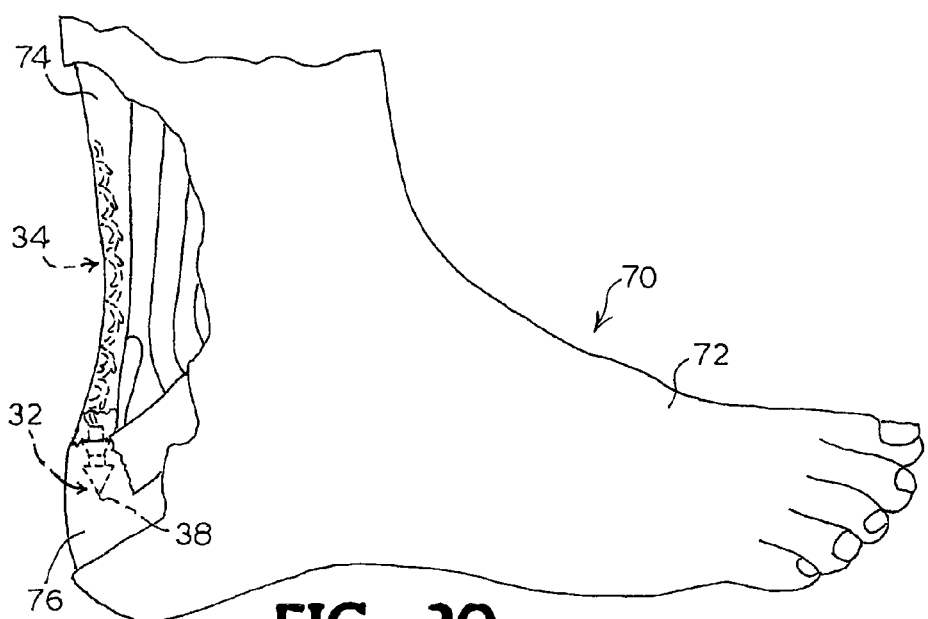

FIGS. 20 and 21 are two views of the Achilles tendon 74 reattached to the heel bone 76 to promote healing according to the present invention using the suture method shown in FIGS. 7-13. The tendon 74 and bone 76 will, over time, grow together.

The present invention provides a compact and easy to use suture anchor and method for reattaching tissue, such as tendons and ligaments, to bone or other connective tissue. The curvilinear placement paths of the suture portion, as contrasted with linear insertion, provide substantially increased biomechanical strength for approximating tissue and bone, or the ends of tendon. The barbed suture portion permits tissue to be approximated and held snug during suturing with less slippage of the suture in the wound. The barbs spread out the holding forces evenly thereby significantly reducing tissue distortion. The suture anchor is useful in endoscopic and arthroscopic procedures and microsurgery. Since knots do not have to be tied, arthroscopic knot tying instruments are unnecessary. If there is an accidental breakage of the barbed suture, the wound is minimally disturbed whereas, with conventional sutures, dehiscence would occur.

Although the present invention has been shown and described in considerable detail with respect to only a few exemplary embodiments thereof, it should be understood by those skilled in the art that we do not intend to limit the invention to the embodiments since various modifications, omissions and additions may be made to the disclosed embodiments without materially departing from the novel teachings and advantages of the invention, particularly in light of the foregoing teachings. For example, the methods of the present invention can be used with a suture anchor alone as a two-way barbed suture. Accordingly, we intend to cover all such modifications, omissions, additions and equivalents as may be included within the spirit and scope of the invention as defined by the following claims.

What is claimed is:

1. A suture system adapted to be positioned in tissue comprising:
   a plurality of sutures, each suture having a first end and a second end;
   a body located between the first ends and the second ends of said plurality of sutures;
   a first plurality of barbs located on each of said suture of the plurality of sutures between the body and the first end;
   each of said first plurality of barbs oriented so as to permit movement of the suture in a direction of movement of the first end through tissue and prevent movement of the suture in a direction of movement of the second end through tissue;
   a second plurality of barbs located on each of said suture of the plurality of sutures between the body and the second end;
   each of said second plurality of barbs oriented so as to permit movement of the suture in a direction of movement of the second end through tissue and prevent movement of the suture in a direction of movement of the first end through tissue; and
   said body connecting together said sutures of said plurality of sutures.

2. The system of claim 1 wherein:
said body is slidably located on said sutures.

3. The system of claim 1 wherein:
said body has an opening and said sutures can slide through said opening.

4. The system of claim 1 wherein:
said body has a first opening and a second opening and said sutures can slid through both said first opening and said second opening.

5. The system of claim 1 wherein:
said body is cylindrical.

6. The system of claim 1 wherein:
said body is a three-dimensional body.

7. The system of claim 1 wherein:
said body includes a bio-absorbable material.

8. The system of claim 1 wherein:
said body includes at least one of ridges, barbs and serrations.

9. The system of claim 1 wherein:
the body has a circular cross-section.

10. The system of claim 1 wherein:
said body includes an opening and said sutures can move relative to said opening.

11. The system of claim 1 wherein:
said body is cone shaped.

12. The system of claim 1 wherein:
said body is wider than any of said sutures.

13. The system of claim 1 wherein:
said body includes an outer surface that can engage and hold tissue.

14. The system of claim 1 wherein:
said body has an outer surface that can hold tissue.

15. The system of claim 1 wherein:
said body is wider than any of said sutures and said body has an outer surface that can hold tissue.

16. The system of claim 1 wherein:
said body includes a first material and said sutures includes a second material; and
said first material is different than said second material.

17. The system of claim 1 wherein:
said first end of each suture is pointed and said second end of each suture is pointed; and
the first pointed ends point away from the body; and
the second pointed ends point away from the body.

18. The system of claim 1 wherein:
said first ends extend away from said body and said second ends extend away from said body.

19. A suture system adapted to be positioned in tissue comprising:
   a plurality of sutures, each suture having a first end and a second end;
   a body located between the first ends and the second ends of said plurality of sutures;
   a first plurality of barbs located on each said suture of the plurality of sutures between the body and the first end;
   each of said first plurality of barbs oriented so as to permit movement of the suture in a direction of movement of the first end through tissue and prevent movement of the suture in a direction of movement of the second end through tissue;
   a second plurality of barbs located on each said suture of the plurality of sutures between the body and the second end;
   each of said second plurality of barbs oriented so as to permit movement of the suture in a direction of movement of the second end through tissue and prevent movement of the suture in a direction of movement of the first end through tissue; and
   said body connecting together said sutures of said plurality of sutures; and
   said body is slidably located on said sutures.

20. A suture system adapted to be positioned in tissue comprising:
   a plurality of sutures, each suture having a first end and a second end;

a body located between the first ends and the second ends of said plurality of sutures;
a first plurality of barbs located on each said suture of the plurality of sutures between the body and the first end;
each of said first plurality of barbs oriented so as to permit movement of the suture in a direction of movement of the first end through tissue and prevent movement of the suture in a direction of movement of the second end through tissue;
a second plurality of barbs located on each said suture of the plurality of sutures between the body and the second end;
each of said second plurality of barbs oriented so as to permit movement of the suture in a direction of movement of the second end through tissue and prevent movement of the suture in a direction of movement of the first end through tissue; and
said body connecting together said sutures of said plurality of sutures; and
said body is slidably located on said sutures; and
said body has an opening and said sutures can move relative to said opening.

\* \* \* \* \*